US012575784B2

(12) United States Patent
Koller et al.

(10) Patent No.: US 12,575,784 B2
(45) Date of Patent: Mar. 17, 2026

(54) DEVICES AND METHODS FOR THE DETECTION OF INTRAORAL ACID EXPOSURE

(71) Applicant: KING'S COLLEGE LONDON, London (GB)

(72) Inventors: Garrit Koller, London (GB); Saoirse O'Toole, London (GB); Timothy Watson, London (GB); Francesco Mannocci, London (GB); David Bartlett, London (GB)

(73) Assignee: KING'S COLLEGE LONDON, London (GB)

( * ) Notice: Subject to any disclaimer, the term of this patent is extended or adjusted under 35 U.S.C. 154(b) by 913 days.

(21) Appl. No.: 17/642,687

(22) PCT Filed: Sep. 11, 2020

(86) PCT No.: PCT/EP2020/075533
§ 371 (c)(1),
(2) Date: Mar. 12, 2022

(87) PCT Pub. No.: WO2021/048396
PCT Pub. Date: Mar. 18, 2021

(65) Prior Publication Data
US 2022/0313152 A1    Oct. 6, 2022

(30) Foreign Application Priority Data
Sep. 12, 2019   (GB) ..................................... 1913208

(51) Int. Cl.
*A61B 5/00*          (2006.01)

(52) U.S. Cl.
CPC .......... *A61B 5/4547* (2013.01); *A61B 5/4211* (2013.01); *A61B 5/4277* (2013.01); *A61B 5/682* (2013.01)

(58) Field of Classification Search
CPC ... A61B 5/4547; A61B 5/4211; A61B 5/4277; A61B 5/682; A61B 5/14539; G01N 31/22
See application file for complete search history.

(56) References Cited

U.S. PATENT DOCUMENTS

2005/0113650 A1 * 5/2005 Pacione ................. A61B 5/165
                                                                    600/300
2006/0116561 A1   6/2006 Tricca et al.
(Continued)

FOREIGN PATENT DOCUMENTS

GB       2321194 A * 7/1998 .......... A61C 13/097
JP     2015192717 A   11/2015
(Continued)

OTHER PUBLICATIONS

Chow LC. Solubility of calcium phosphates. Monogr Oral Sci. 2001;18:94-111. doi: 10.1159/000061650. PMID: 11758450.
(Continued)

*Primary Examiner* — Jacqueline Cheng
*Assistant Examiner* — Tho Q Tran
(74) *Attorney, Agent, or Firm* — Tarolli, Sundheim, Covell & Tummino LLP

(57) ABSTRACT

The present invention provides non-invasive intraoral devices and methods for the detection of intraoral acid exposure, methods of making said devices, and their use in the diagnosis of disorders such as gastro-oesophageal reflux disease (GORD).

25 Claims, 8 Drawing Sheets

(56) References Cited

U.S. PATENT DOCUMENTS

| | | | | |
|---|---|---|---|---|
| 2007/0207440 A1* | 9/2007 | Chen | | A61C 7/00 |
| | | | | 433/106 |
| 2015/0374274 A1* | 12/2015 | Jovanovski | | A61B 5/4211 |
| | | | | 600/309 |
| 2016/0202137 A1 | 7/2016 | Shi et al. | | |
| 2017/0039893 A1 | 2/2017 | Drake et al. | | |
| 2018/0020957 A1* | 1/2018 | Kinser | | A61B 5/14532 |
| | | | | 600/347 |
| 2018/0368766 A1 | 12/2018 | Keels | | |
| 2019/0223751 A1 | 7/2019 | Weinstein et al. | | |

FOREIGN PATENT DOCUMENTS

| | | |
|---|---|---|
| KR | 20180099101 A | 9/2018 |
| WO | 2011028758 A2 | 3/2011 |

OTHER PUBLICATIONS

Yadlapati R, Adkins C, Jaiyeola DM, Lidder AK, Gawron AJ, Tan BK, Shabeeb N, Price CP, Agrawal N, Ellenbogen M, Smith SS, Bove M, Pandolfino JE. Abilities of Oropharyngeal pH Tests and Salivary Pepsin Analysis to Discriminate Between Asymptomatic Volunteers and Subjects With Symptoms of Laryngeal Irritation. Clin Gastroenterol Hepatol. Apr. 2016;14(4):535-542.e2. doi: 10.1016/j.cgh.2015.11.017. Epub Dec. 9, 2015. PMID: 26689899; PMCID: PMC4799733.

Huang J, Li X, Koller GP, Di Silvio L, Vargas-Reus MA, Allaker RP. Electrohydrodynamic deposition of nanotitanium doped hydroxyapatite coating for medical and dental applications. J Mater Sci Mater Med. Mar. 2011;22(3):491-6. doi: 10.1007/s10856-010-4226-y. Epub Jan. 18, 2011. PMID: 21243517.

Tolia V, Vandenplas Y. Systematic review: the extra-oesophageal symptoms of gastro-oesophageal reflux disease in children. Aliment Pharmacol Ther. Feb. 1, 2009;29(3):258-72. doi: 10.1111/j.1365-2036.2008.03879.x. PMID: 19143046.

Chang AB, Lasserson TJ, Kiljander TO, Connor FL, Gaffney JT, Garske LA. Systematic review and meta-analysis of randomised controlled trials of gastro-oesophageal reflux interventions for chronic cough associated with gastro-oesophageal reflux. BMJ. Jan. 7, 2006;332(7532):11-7. doi: 10.1136/bmj.38677.559005.55. Epub Dec. 5, 2005. PMID: 16330475; PMCID: PMC1325125.

De Jonge PJ, van Blankenstein M, Grady WM, Kuipers EJ. Barrett's oesophagus: epidemiology, cancer risk and implications for management. Gut. Jan. 2014;63(1):191-202. doi: 10.1136/gutjnl-2013-305490. Epub Oct. 3, 2013. PMID: 24092861; PMCID: PMC6597262.

El-Serag HB, Sweet S, Winchester CC, Dent J. Update on the epidemiology of gastro-oesophageal reflux disease: a systematic review. Gut. Jun. 2014;63(6):871-80. doi: 10.1136/gutjnl-2012-304269. Epub Jul. 13, 2013. PMID: 23853213; PMCID: PMC4046948.

Kaplan M, Tanoglu A, Erkul E, Kara M, Yazgan Y. Association of reflux symptom index scores with gastroesophageal flap valve status. Auris Nasus Larynx. Dec. 2014;41(6):543-7. doi: 10.1016/j.anl.2014.05.006. Epub Jun. 2, 2014. PMID: 24889495.

Bartlett D. A personal perspective and update on erosive tooth wear—10 years on: Part 2—Restorative management. Br Dent J. Aug. 26, 2016;221(4):167-71. doi: 10.1038/sj.bdj.2016.596. PMID: 27561573.

Bartlett DW, Evans DF, Anggiansah A, Smith BG. A study of the association between gastro-oesophageal reflux and palatal dental erosion. Br Dent J. Aug. 24, 1996;181(4):125-31. doi: 10.1038/sj.bdj.4809187. PMID: 8840581.

S. O'Toole, M. Pennington, S. Varma, D.W. Bartlett, The treatment need and associated cost of erosive tooth wear rehabilitation—a service evaluation within an NHS dental hospital, BDJ. 224 (2018) 957-961. doi:10.1038/sj.bdj.2018.444.

O'Toole S, Bernabe E, Moazzez R, Bartlett D. Timing of dietary acid intake and erosive tooth wear: A case-control study. J Dent. Jan. 2017;56:99-104. doi: 10.1016/j.jdent.2016.11.005. Epub Nov. 14, 2016. PMID: 27856311.

Vaezi MF, Sifrim D. Assessing Old and New Diagnostic Tests for Gastroesophageal Reflux Disease. Gastroenterology. Jan. 2018;154(2):289-301. doi: 10.1053/j.gastro.2017.07.040. Epub Aug. 1, 2017. PMID: 28774844.

Dorozhkin SV. Surface Reactions of Apatite Dissolution. J Colloid Interface Sci. Jul. 15, 1997;191(2):489-97. doi: 10.1006/jcis.1997.4942. PMID: 9268533.

Trombetta R, Inzana JA, Schwarz EM, Kates SL, Awad HA. 3D Printing of Calcium Phosphate Ceramics for Bone Tissue Engineering and Drug Delivery. Ann Biomed Eng. Jan. 2017;45(1):23-44. doi: 10.1007/s10439-016-1678-3. Epub Jun. 20, 2016. PMID: 27324800; PMCID: PMC5173433.

Mylonas P, Austin RS, Moazzez R, Joiner A, Bartlett DW. In vitro evaluation of the early erosive lesion in polished and natural human enamel. Dent Mater. Sep. 2018;34(9):1391-1400. doi: 10.1016/j.dental.2018.06.018. Epub Jul. 7, 2018. PMID: 30131115.

Rodriguez JM, Austin RS, Bartlett DW. In vivo measurements of tooth wear over 12 months. Caries Res. 2012;46(1):9-15. doi: 10.1159/000334786. Epub Dec. 10, 2011. PMID: 22156738.

Kocak, G., C. Tuncer, and V. Bütün. "pH-responsive polymers. Polym Chem 8: 144-176." (2017).

Feenstra, T. P., and P. L. De Bruyn. "Formation of calcium phosphates in moderately supersaturated solutions." Journal of Physical Chemistry 83.4 (1979): 475-479.

Bohner M. Calcium orthophosphates in medicine: from ceramics to calcium phosphate cements. Injury. Dec. 2000;31 Suppl 4:37-47. doi: 10.1016/s0020-1383(00)80022-4. PMID: 11270080.

Dorozhkin SV, Epple M. Biological and medical significance of calcium phosphates. Angew Chem Int Ed Engl. Sep. 2, 2002;41(17):3130-46. doi: 10.1002/1521-3773(Sep. 2, 2002)41:17<3130::AID-ANIE3130>3.0.CO;2-1. PMID: 12207375.

Combes C, Rey C. Amorphous calcium phosphates: synthesis, properties and uses in biomaterials. Acta Biomater. Sep. 2010;6(9):3362-78. doi: 10.1016/j.actbio.2010.02.017. Epub Feb. 16, 2010. PMID: 20167295.

Haldeman, Keene O., and John M. Moore. "Influence of a local excess of calcium and phosphorus on the healing of fractures: an experimental study." Archives of Surgery 29.3 (1934): 385-396.

Tamimi, Faleh, et al. "Brushite-collagen composites for bone regeneration." Acta Biomaterialia 4.5 (2008): 1315-1321.

Daculsi, G., et al. "Biphasic calcium phosphate/hydrosoluble polymer composites: a new concept for bone and dental substitution biomaterials." Bone 25.2 (1999): 59S-61S.

LeGeros, R. Z. "Calcium phosphate materials in restorative dentistry: a review." Advances in dental research 2.1 (1988): 164-180.

Peptest "https://www.peptest.co.uk/" RDBiomed Limited Castle Hill Hospital Daisy Building (2nd Floor) Castle Road, Cottingham HU16 5JQ, UK, VAT No. GB 990 1918 96.

International Search Report and Written Opinion mailed Dec. 21, 2020 for corresponding International Application No. PCT/EP2020/075533.

* cited by examiner

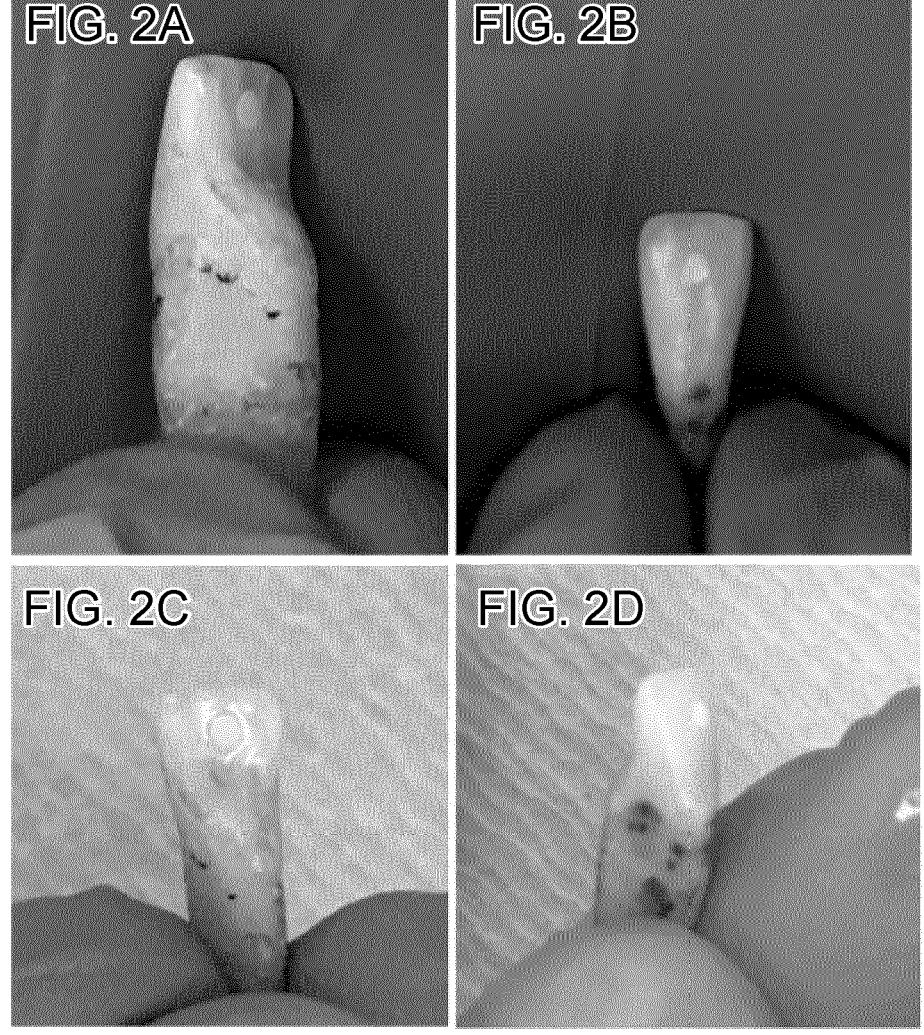
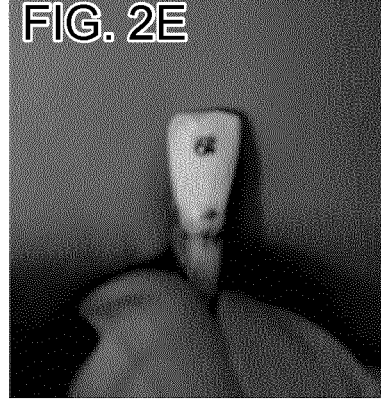
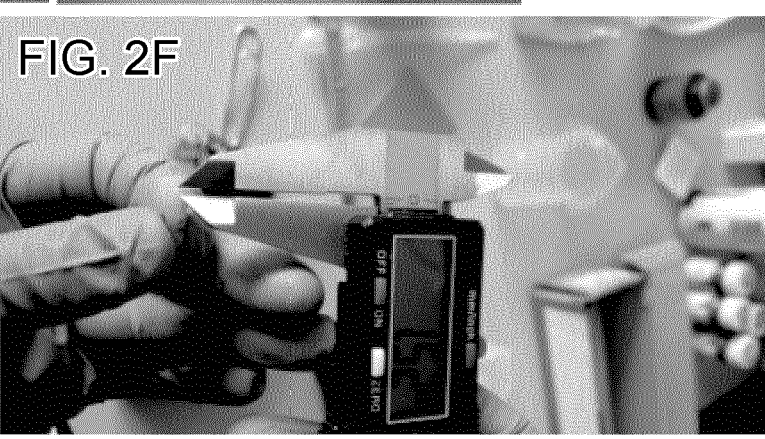

Flow chart for acid exposure protocol

DEVICES AND METHODS FOR THE DETECTION OF INTRAORAL ACID EXPOSURE

RELATED APPLICATIONS

The present application is a U.S. National Stage application under 35 USC 371 of PCT Application Serial No. PCT/EP2020/075533, filed on 11 Sep. 2020; which claims priority from GB Patent Application No. 1913208.3, filed 12 Sep. 2019, the entirety of both of which are incorporated herein by reference.

FIELD OF THE INVENTION

The present invention relates to non-invasive intraoral devices and methods. In particular, the present invention relates to non-invasive intraoral devices and methods for the detection of intraoral acid exposure and to non-invasive intraoral devices and methods for the detection of pathological acid tooth erosion. The invention further relates to methods of making said devices, and to their use in the diagnosis of disorders such as gastro-oesophageal reflux disease (GORD).

BACKGROUND

Erosive tooth wear is the chemical and/or mechanical wear of dental hard tissues. It may be physiological, resulting from normal use and function, or pathological, where it negatively affects function, aesthetics and can cause severe dental hypersensitivity if not identified and treated early.

In addition to the impact on individuals affected with erosive tooth wear, the treatment of severe erosive tooth wear is extensive and expensive [8]. Interestingly, fear of erosive tooth wear progression was the most common reason recorded for seeking treatment [8].

In the majority of cases of severe tooth wear, there is an acidic component in the aetiology [6] and erosive tooth wear is a recognised side effect of gastric reflux [7]. There are multiple case reports published in dental journals whereby dentists were the first health care practitioners to diagnose underlying gastro-intestinal conditions after years of careful assessment and follow up and were able to ensure appropriate care was provided for the patient.

However, the source of the acid may also be extrinsic. The interplay of chemical, biological and behavioural factors is complex and helps explain why some individuals exhibit more erosion than others [9]. Diagnosis of early forms of erosion is difficult, as it is accompanied by few signs and fewer, if any, symptoms. General dental practitioners (GDP's) currently have no accurate, quantitative method to determine whether the tooth wear is a result of dietary acids, whereupon the treatment is dietary advice, or gastric reflux which should be referred to a medical doctor for assessment.

Furthermore, as tooth wear is irreversible, there is also no method to establish whether the wear is active or historical.

Clinical appearance is the most important feature for dental professionals to diagnose this condition. In primary care, disease activity is currently assessed by recording clinical indices at interval appointments. The Basic Erosive Wear Examination (BEWE) was developed by expert consensus in 2008 and is becoming increasingly adopted by GDP's and epidemiological researchers. An alternative method is to take dental study casts at interval appointments and inspect them for differences. The literature suggests that it takes a minimum of 18-24 months of disease activity to occur to detect clinical differences. Both of these methods are heavily subjective and rely upon a long-term relationship between a patient and the same dentist. If a dentist has a concern whether there is an underlying pathological condition, the diet must first be stabilised before the assessment of whether additional erosive wear is occurring can be made.

Extra-oesophageal reflux (reflux) is understood to be the retrograde flow of gastric contents, for example, into the oral cavity, oropharynx, larynx and/or the nasopharynx. Gastric contents may comprise a number of constituents including hydrochloric acid and digestive enzymes (such as peptidases, for example, trypsin). Reflux is implicated as a symptom or underlying cause of a number of pathologies, these include gastro-oesophageal reflux disease (GORD) and erosive tooth wear.

GORD is the frequent leakage of gastric contents into the oesophagus. The prevalence of GORD in Europe is approximately 8.8%-25.9% [1]. Symptoms are not always present and there is little correlation between symptoms and disease severity [2]. Approximately 5% of those suffering from GORD will develop Barrett's oesophagitis, a pre-malignant form of adenocarcinoma and 0.1-0.5% will develop oesophageal adenocarcinoma [3]. The UK has one of the highest prevalence of silent reflux and Barrett's oesophagitis.

Furthermore, reflux is common in patients with respiratory disease, with a prevalence as high as 50% in patients with chronic cough, severe chronic obstructive pulmonary disorder (COPD) and difficult to control asthma [4,5]. However, the evidence behind whether reflux directly contributes to respiratory disease is unclear as there is currently no accurate or sensitive test for extra-oesophageal reflux. Similarly, asymptomatic gastro-oesophageal reflux disease (GORD) can lead to severe inflammation of the oesophagus and possibly in malignant changes [3]. When diagnosed late, the prognosis is poor and treatment extensive. The presence of hydrochloric acid entering the oral cavity has potential to be a signal indicative of extra-oesophageal reflux disease and asymptomatic GORD. Increasingly, acid reflux is being recognised as an aetiological factor in multiple respiratory symptoms.

Initial treatment plans for acid reflux are generally based upon patient symptoms, with very few objective clinical signs. This has often resulted in anti-reflux drugs being administered as a diagnostic tool in patients with recalcitrant symptoms [10]. The main initial treatment is a stay-and-play approach with empirical dosing and dose escalation of proton pump inhibitors (with or without further medication such as domperidone). Referral threshold is reached if the symptoms do not resolve or progress. Subsequent testing is invasive, costly and moderately sensitive including imaging studies, such as gastroscopy and barium meals.

Research in the gastroenterology field is currently focused on salivary biomarkers (predominantly pepsin) as a method of detecting active gastric reflux from the oral cavity. However, the detection of salivary biomarkers is not a straightforward mechanism. There is large individual variation and a translatable chairside application is far from feasible currently [11]. There is also research in the gastroenterology field on less invasive forms of pH monitoring, such as wireless pH monitoring and impedance pH monitoring. However, this highly specialised and costly equipment must be used by trained health practitioners in specialist settings and is associated with significant discomfort to the patient during these investigations.

Within the medical field, a non-invasive device diagnosing intraoral acid exposure, e.g. a non-invasive intraoral device, and straightforward method of use, which can be applied without prior training, would therefore present a much-needed adjunct to the complex decision making in primary care surrounding reflux testing and treatment.

More generally, a non-invasive method for the early detection of acidic tooth erosion and/or to determine whether erosion is the result of dietary or gastric acids, would represent a significant contribution to the art.

SUMMARY OF THE INVENTION

The present invention is based on the realisation by the present inventors that the presence and specific persistence of causative acids in tooth wear, such as hydrochloric acid entering the oral cavity has the potential to be a signal diagnostic for extra-oesophageal reflux disease and asymptomatic GORD.

The devices and methods of the invention will allow any health care professional to assess for extra-oesophageal reflux within a short time for specific diagnosis and to determine specific disease activity such as response to an intervention. For the first time, primary care professionals will be able to categorise the risk based upon the patient's chemical, biological and behavioural risk factors, improving the decision making process for complex treatment plans.

This innovation provides, for the first time, an accurate method of extra-oesophageal testing which will be non-invasive, cheap and highly selective. There is currently no other approach in use within primary, secondary or tertiary care that can determine disease activity and indicate the source of the acid damage. This will result in more timely referrals for medical investigations and patient empowerment to monitor and control their own disease progression.

Advantageously, the devices and methods of the invention can also be adapted for the detection of dietary acids, in addition, or as an alternative, to the detection of mineral acids.

The potential to differentiate between the effects of gastric (mineral) and dietary (organic) acids is a significant advantage of the devices and methods described herein.

Acid-Sensing Device

Accordingly, one aspect of the present invention provides an oral acid-sensing device for fixation to a surface of a tooth within the oral cavity of a subject.

The device of the invention includes at least one erodible layer.

At least one erodible layer is preferably arranged to be in direct contact with saliva when the device is in situ within the oral cavity. In some embodiments, this layer may be described as the 'top' layer, because it is the uppermost or outermost layer i.e. the distal layer relative to the tooth surface to which the device is affixed, when the device is in use. However, it will be understood that the absolute orientation of the device may vary and that terms such as 'top', 'bottom', 'upper', 'lower', 'above', 'beneath', etc, as used in the context of the layer(s) in the present device, are not intended to be limiting in that regard.

The erodible layer is formed of, or comprises, an erodible material. The erodible material erodes (dissolves) in the presence of an acidic medium e.g. in the presence of intraoral acids. Dissolution of the erodible material from the erodible layer is visually detectable e.g. as further described below.

The erodible material may be selected so as to have an erosion (dissolution) rate, in the presence of an acidic medium, which is significantly faster than the erosion rate of natural dental enamel, when contacted with an identical acidic medium. In preferred embodiments, the erodible material in the upper layers is selected to selectively dissolve in the presence of mineral acids, but is relatively insoluble in organic acids at concentrations encountered in the diet. Properties of the erodible material are described in more detail below.

In other embodiments, the erodible layer may undergo a visible change, i.e. a colour change, as a result of dissolution/erosion of the erodible material. In preferred embodiments, the rate of this colour change is greater than the rate of any colour change produced in natural dental enamel due to erosion with an identical acidic medium.

The device of the invention further comprises an indicator. Properties of the indicator are discussed in more detail below.

The indicator is preferably a visual indicator. In some preferred embodiments, the indicator is in a separate layer, located beneath the top layer (i.e. closer to the tooth surface, when in use). In these embodiments, the indicator layer is initially covered by the top layer (and optionally, by one or more intervening layers to give a semi-quantitative method of measuring acid activity). Erosion of the top layer (e.g. by acidic media present in the oral cavity) hence exposes the indicator layer, making it visible to inspection and hence providing a response from said indicator.

In other embodiments, as noted above, the erodible layer may itself serve as the indicator, producing a visible change (in particular a colour change) as a result of its erosion/dissolution.

In some embodiments, the device further comprises additional layers beneath the top layer. In some embodiments, said additional layers are in addition to said indicator layer. Any or each of these layers may comprise an erodible material, which may the same as or different to the erodible material in the top layer. Any or each of these additional layers may also comprise a further indicator.

In some embodiments, the layers making up the sensing device are housed in a pre-formed bracket, which is preferably formed of a composite material.

Methods of Use

Another aspect of the present invention provides a method of detecting the presence of acid (for example, gastric and/or dietary acid) within the oral cavity. The method involves applying an oral acid-sensing device as described herein to a tooth surface within the oral cavity of a subject and monitoring the device, over a suitable time period, to determine the response from the indicator layer.

A further aspect of the present invention is a method of diagnosing a disease or condition characterised by pathological erosive tooth wear and/or characterised by the presence of mineral acid within the oral cavity. Such diseases or conditions include, but are not limited to, gastro-oesophageal reflux disease (GORD), extra-oesophageal reflux disease, chronic cough, chronic obstructive pulmonary disease, severe asthma, bulimia, and erosive tooth wear. The methods involve application of an oral acid-sensing device as described herein to a tooth surface within the oral cavity of a subject and monitoring the device, over a suitable time period, to determine a response from the indicator layer. In these methods, a positive response from the indicator layer may be suggestive of the presence of said disease or condition.

In some embodiments, the sensing device is housed in a pre-formed bracket, which is preferably formed of a resin-based oligomer matrix material. Application of the device may therefore be achieved via fixation of the bracket to a tooth surface, using standard dental adhesives and techniques.

Methods of Manufacture

A further aspect of the present invention provides a method of making an oral acid-sensing device as described herein.

In one embodiment, said method includes a step of 3D printing and/or milling, for example of a resin-based matrix system.

In some embodiments, the method includes at least one step of chemical deposition of an erodible layer (for example a calcium phosphate) and/or an indicator layer.

In some embodiments, the method includes at least one step of sintering of the components and/or of the assembled layers.

BRIEF DESCRIPTION OF THE FIGURES

FIG. 2: Prototype device, showing device temporarily bonded to the palatal surface of an extracted lower incisor tooth (FIG. 2A) and the buccal surface of a lower incisor tooth (FIG. 2B), and corresponding views from different angles (FIGS. 2C and 2D). FIG. 2E demonstrates the prototype after dissolution in HCl. FIG. 2F measures the device at 1.5 mm in diameter.

DETAILED DESCRIPTION OF THE INVENTION

Figure 1:
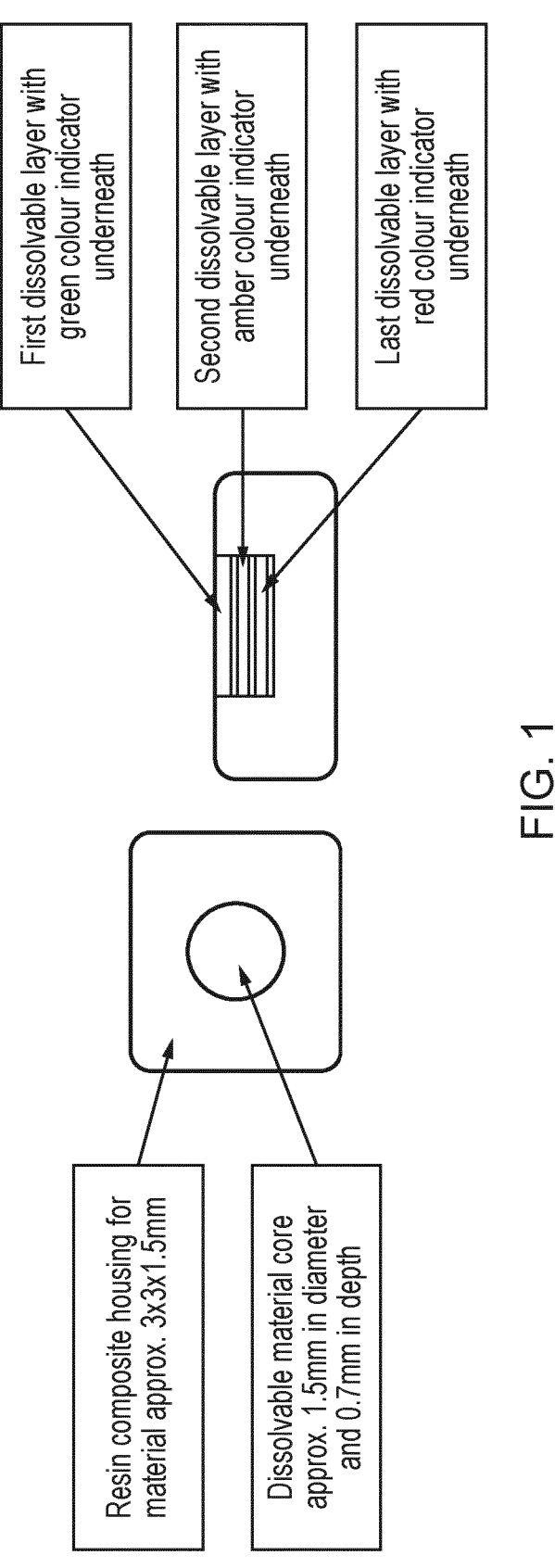
FIG. 1: Schematic diagrams of the proposed device in surface view and cross section including gradients and domed designs.

Aspects and embodiments of the present invention will now be discussed with reference to the accompanying figures. Further aspects and embodiments will be apparent to those skilled in the art. All documents mentioned in this text are incorporated herein by reference.

Acid-Sensing Device

The acid sensing device of the present invention includes at least one layer comprising an erodible material. The acid sensing device of the present invention also includes at least one layer which acts as, or comprises, an indicator. The erodible layer (i.e. the layer comprising, or formed of, the erodible material) and the indicator layer (i.e. the layer which acts as, or comprises, an indicator) may be separate layers or they may form part of the same layer. In some embodiments, the acid sensing device of the present invention includes at least one layer of an erodible material. At least one of the layers contains an indicator.

The device is for use within the oral cavity of a subject, wherein in use the device is contacted by the saliva of the subject within the oral cavity of the subject. The presence of acid is detected through the loss (erosion) of one or more layers or portions of the layers of the device when in use, producing a response from the indicator.

The devices of the invention are thin and preferably multi-layered, and are optionally housed in a pre-formed composite bracket which can be applied to a non-visible tooth surface. These can be reversibly bonded, for example by means of self-etch adhesives, by any trained healthcare professional to a tooth surface that will cause minimal disruption to the patient.

In preferred embodiments, the devices of the invention comprise a thin, optionally multi-layered, erodible material, optionally housed in said pre-formed composite bracket. The erodible material selected such that it will only dissolve in the presence of acid (in some embodiments, only in the presence of a mineral acid e.g. hydrochloric acid), thus exposing an indicator (e.g. a pigment) underneath. In preferred embodiments this provides a simple colour readout if said acid is present in the oral cavity, which may indicate e.g. that there is active disease. In some preferred embodiments, the erodible material is, or comprises, a calcium phosphate composition.

In these embodiments, in the case that the device has more than one layer, the top layer (i.e. exposed to the oral cavity, farthest from the surface of the tooth when affixed in the oral cavity) preferably does not contain an indicator, but the lower layer or layers may contain an indicator. The erosion of the top layer, and subsequent deeper layers, exposes the indicator which provides a semi-quantitative guide, indicative of the acid activity in the oral cavity.

In one such embodiment, the device contains two layers. The top (erodible) layer comprises the erodible material but does not comprise an indicator; the second layer does comprise an indicator. Erosion of the top layer when in use leads to exposure of the second layer and therefore the indicator, exposure of the indicator leads to a visual response indicating the presence of acid.

Although multi-layered devices are preferred, in some embodiments, the device may have only one layer. In some embodiments, said layer is an erodible layer, for example a calcium phosphate containing layer, and also comprises an indicator. Loss of the indicator signal when in use (e.g. depletion of visible colour) would then denote erosion of the single layer and therefore the presence of acid in the oral cavity. In alternative single-layered embodiments, the erodible layer undergoes a visible change, i.e. a colour change, as a result of dissolution/erosion of the erodible material. In these embodiments a separate indicator is not required as it is inherent in the erodible layer itself.

The nature and properties of the erodible layer can be adjusted to tailor the device to the detection and frequency of exposure to particular acids. For example for the detection of mineral acids, such as stomach acid which may enter the mouth as a result of gastric reflux or vomiting or organic acids, such as citric acid which may arise from dietary sources. Alternatively the device could be composed of a material which is configured to detect both classes of acid equally well.

In some embodiments, the invention therefore provides devices which utilise differential dissolution rates of erodible layers in mineral acids versus organic acids to distinguish the presence of mineral acid in the oral cavity over that of dietary acids. When mineral acid is present, a first erodible layer is dissolved more rapidly than in the absence of mineral acid, exposing a second indicator layer. Exposure of the indicator layer within a predefined time limit denotes the presence of mineral acid.

In a particularly preferred embodiment, a device of the invention comprises a composite bracket (similar to an orthodontic bracket), applicable to a susceptible tooth surface (for example by means of temporary self-etch adhesives such as those used for cosmetic tooth jewellery). Within the composite bracket is a layered indicator phase, comprising multiple, differentially coloured sacrificial layers, which are removed by acid at a higher rate than hydroxyapatite (HA) in naturally occurring tooth enamel would be removed. Thus a sensitive and specific test is presented for the presence and rate of acid exposure on the appropriate surfaces.

By the choice of erodible material, the susceptibility and sensitivity of the device may be tailored and adjusted, whilst maintaining relevance to the biological substrate of teeth, hydroxyapatite, being eroded. One simple preferred embodiment comprises a single, coloured/pigmented layer under a white or tooth-coloured, defined thickness, erodible layer (for example, a calcium phosphate layer). However, various resistances may be engineered by the choice of sacrificial material layer (e.g. by the choice of CaP composition or combination). In other embodiments, the reactivity and/or sensitivity of the superficial layer or erodible material can be tailored.

Application of the device for a suitable period would give the dentist or patient a simple colour read-out of whether sufficient acid exposure had occurred to erode the clear surface layer to reveal the coloured indicator layer. This may be adapted to a quantitative test by the incorporation of multiple layers with differential chemistries, to quantify the frequency and severity of acid attack by assessing the colour against an index.

Erodible Layer/Erodible Material

As used herein, the term 'erodible' means that the material or layer is gradually consumed (i.e. dissolved) in the presence of an acidic medium, specifically a medium that has a pH below pH at which Dental Enamel or Dentine may dissolve, i.e. pH 6.4. This means that a layer composed of the erodible material, upon exposure to said acidic medium, will gradually reduce in thickness and will eventually be wholly or partly removed, due to dissolution (erosion) of the material. Alternatively or additionally, a layer comprising the erodible material, upon exposure to said acidic medium, may produce a visually perceptible change of physical characteristics (including, for example, a change of colour) due to dissolution (erosion) of the material.

The erodible material for use in the erodible layer(s) in the devices of the invention preferably has a dissolution rate, in the presence of an acidic medium, which is significantly greater than the dissolution rate of natural dental enamel, when contacted with an identical acidic medium. Alternatively or additionally, the erodible layer has a rate of colour change due to dissolution of the erodible material which is greater than the rate of colour change produced in natural dental enamel by the same acidic medium. In preferred embodiments, the erodible material in the erodible layer(s) is selected to selectively dissolve in the presence of mineral acids, but is relatively insoluble in organic acids at concentrations encountered in the diet.

Suitable erodible materials are biocompatible and are stable in thin cross-section. Examples include, but are not limited to, calcium phosphate compositions (the chemical and physical properties of which can be tailored to provide the required rates of erosion, as discussed further below), pH sensitive polymers such as polymeric carboxylic acids and phosphonic acids, or natural polymers such as hyaluronic acid, chitosan or dextran. For instance, Kocak and coworkers disclose the use of poly(methacrylic acid) polymers to selectively break down at pH<6.4. [12]

The material may be, in turn, treated with a sacrificial chemical treatment, such as oxalic acid, to delay or reduce erosion.

Solubility/Dissolution Rate

The material in the erodible layer(s) is preferably selected so as to have an erosion (dissolution) rate, in the presence of an acidic medium, which is significantly faster than the erosion rate of natural dental enamel in an identical acidic medium. This allows the device to detect the presence of acid in the oral cavity over a short test period.

In some embodiments, the material in the erodible layer(s) has a dissolution rate in an acidic medium which is at least ten times faster than the dissolution rate of natural dental enamel in the same acidic medium.

In some embodiments, the material in the erodible layer(s) has a dissolution rate in an acidic medium which is at least twenty times faster than the dissolution rate of natural dental enamel in the same acidic medium.

In some embodiments, the material in the erodible layer(s) has a dissolution rate in an acidic medium which is at least thirty times faster than the dissolution rate of natural dental enamel in the same acidic medium.

In some embodiments, the material in the erodible layer(s) has a dissolution rate in an acidic medium which is at least 50 times faster than the dissolution rate of natural dental enamel in the same acidic medium.

In some embodiments, the material in the erodible layer(s) has a dissolution rate in an acidic medium which is at least a hundred times faster than the dissolution rate of natural dental enamel in the same acidic medium.

In some embodiments, the material in the erodible layer(s) has a dissolution rate in an acidic medium which is up to 150 times faster than the dissolution rate of natural dental enamel in the same acidic medium.

In some embodiments, the material in the erodible layer(s) has a dissolution rate in an acidic medium which is up to 200 times faster than the dissolution rate of natural dental enamel in the same acidic medium.

In some embodiments, the material in the erodible layer(s) has a dissolution rate in an acidic medium which is from 10 to 200 times faster than the dissolution rate of natural dental enamel in the same acidic medium.

In some embodiments, the material in the erodible layer(s) has a dissolution rate in an acidic medium which is from 20 to 150 times faster than the dissolution rate of natural dental enamel in the same acidic medium.

In some embodiments, the material in the erodible layer(s) has a dissolution rate in an acidic medium which is from 30 to 150 times faster than the dissolution rate of natural dental enamel in the same acidic medium.

Dissolution rate, as used herein, is a measure of the mass of solid material consumed (i.e. entering solution) as a function of time. Relative dissolution rate for a particular material could be assessed, for example, by comparing the time taken to fully dissolve a sample of the material with the time taken to fully dissolve an equivalent sample of simulated or natural dental enamel.

Dissolution rate may also be assessed by measuring the depth of erosion (profilometric loss) of a surface of known surface area, composed of the relevant solid material. Profilometric loss due to erosion can be assessed, for example, using confocal laser profilometry. Surface roughness changes, as also measured using profilometry, can be used as an indicator of early erosive changes and also increased susceptibility to further acid challenges. [13]

In some embodiments, dissolution of the erodible material by an acidic medium results in a colour change of the erodible layer. The rate of this colour change is preferably greater than the rate of any corresponding colour change in natural dental enamel. Colour change and/or rate of colour change may be assessed or measured, for example by use of a colorimeter, as is known in the art.

Natural dental enamel is an inorganic substance with a high mineral component and contains circa 96% substituted calcium hydroxyapatite, 3% water and 1% organic material with calcium and carbonate substitutions. There are also low concentrations of sodium, magnesium, chloride, potassium and other trace elements. It is present in specific, approximately 70 nm crystals with structures and alignment to resist chemo/mechanical challenges and stresses.

Human enamel wears (erodes) at a relatively low rate. Human enamel also changes colour at a relatively low rate. Even under pathological conditions, it has been demonstrated that a rate of erosion of over 100 microns over 6 months could be expected. [14] In contrast, the present inventors have demonstrated that acid exposure which would equate to a physiologically relevant moderate acid challenge (3×10 minute acid exposure) produced less than 2 microns of loss in natural enamel, compared to 30 microns of loss in an exemplary erodible layer according to the invention (comprising β-TCP).

In some preferred embodiments, the erodible layer(s) in the proposed device will dissolve at a rate 30-150 times that of natural human enamel.

Without wishing to be bound by theory, the erodible materials used in the devices of the present invention dissolve (erode) at a significantly faster rate than natural enamel because of their physical and chemical properties.

For example, in some embodiments, factors including but not limited to the type and form of the material, its particulate chemistry, its surface roughness, and the density of the material, may all affect its rate of dissolution in acidic media. More specifically, for example, in a calcium phosphate erodible layer the type and form of calcium phosphate present, its particulate chemistry, surface roughness, and density of the calcium phosphate composition all play a role. For example, higher surface roughness may result in more erosion because it increases the surface area for interaction with acid; as calcium phosphates tend to erode in pits and fissures, this can also influence the penetration of the acid.

An erodible material having the required dissolution rate and/or rate of colour change can hence be provided, by tailoring the physical and chemical properties of the material, as would be understood by the person skilled in the art.

Acidic media is for example an aqueous solution with an acidic pH (i.e. less than pH 7). The acidic medium by which the erodible layer is erodible (i.e. in which it dissolves) may comprise mineral and/or organic acids.

Selectivity for Mineral Acids

In some embodiments, the erodible material in at least one erodible layer is selected to selectively dissolve in the presence of mineral acids, but is relatively insoluble (or dissolves relatively slowly) in organic acids.

In some embodiments, the erodible layer(s) of the device are dissolved at a faster rate by mineral acid solutions than organic acid solutions.

In some embodiments, the material in the erodible layers has a dissolution rate in mineral acids which is significantly faster than its dissolution rate in organic acids.

In some embodiments, the material in the erodible layers has a dissolution rate in mineral acids which is at least 10 times faster than its dissolution rate in organic acids.

In some embodiments, the material in the erodible layers has a dissolution rate in mineral acids which is at least 75 times faster than its dissolution rate in organic acids.

In some embodiments, the material in the erodible layers has a dissolution rate in mineral acids which is at least 100 times faster than its dissolution rate in organic acids.

Mineral acids are inorganic compounds which can readily dissociate into hydrogen ions and a conjugate base when dissolved in water. Examples of mineral acids include, but are not limited to: hydrochloric acid, nitric acid, phosphoric acid, sulfuric acid, boric acid, hydrofluoric acid, hydrobromic acid, hydroiodic acid, and perchloric acid.

Organic acids, particularly those derived from dietary sources, include, but are not limited to: citric acid, lactic acid, glutamic acid, acetic acid, ascorbic acid, carbonic acid, malic acid, oxalic acid, aldonic acids, ulosonic acids, uronic acids, and aldaric acids.

The dissolution rates of erodible materials in the devices as described herein, in mineral and organic acid solutions may be independent of pH (especially intraorally). Saliva and the salivary pellicle has been observed to offer better protection against citric acid than hydrochloric acid.

In the case of calcium phosphate based erodible layers, without wishing to be bound by theory, it is thought that the chelation of calcium ions in the calcium phosphate phase by carboxylate counter ions in organic acids may result in deposition of calcium compounds on the surface of the material, stabilising the Nernst layer and slowing the rate of dissolution whilst reducing the mechanical integrity of the bulk material.

In other embodiments, as the skilled person would appreciate, aspects of their chemistry may be exploited to dissolve at different rates in strong and weak acids. For example oxalic acid, a dicarboxylic acid, shows a negligible affinity and poor dissolution in citric acid but would be rapidly dissolved in hydrochloric acid.

In some embodiments, the higher solubility of the erodible layer(s) in mineral acids as compared to organic acids allows the presence of mineral acids to be ascertained selectively. This allows the diagnosis of pathological erosion (as opposed to erosion caused by diet or behavioural factors). However, in some embodiments the devices of the invention may also be used to diagnose the presence of excess organic (dietary) acids.

Hence, in some embodiments, the primary aim of the devices and methods of the invention is to identify the presence of mineral acids but, if mineral acids are NOT present, a secondary function is to assess the acidity of the diet. It may be important to be able to recognise if certain behaviours will cause long term damage to teeth e.g. acidic medications or a professional wine taster.

Erodible Material

The erodible layer(s) in the devices of the invention are formed of, or comprise, erodible materials. As used herein, the term 'erodible material' may encompass any material, substance, compound, or composition which dissolves (erodes) in an acidic medium. The term 'erodible layer' may encompass any layer comprising such an erodible material as part of its structure or composition.

In some embodiments, the erodible material is, or comprises, a calcium phosphate composition, as further described below. In some embodiments, the erodible material is, or comprises, a pH sensitive polymer such as carboxylic acids, phosphonic acids or natural polymers such as hyaluronic acid, chitosan or dextran as further described herein.

Calcium Phosphate Compositions for Use as Erodible Materials

Calcium phosphate (CaP) materials are currently used in preventive and restorative dentistry and have the potential for both dental and medical applications. [16, 17] They are of special interest due to their biocompatibility and biodegradability. [18]

Amorphous calcium phosphate (ACP) has been widely applied in dental or oral science due to its excellent bioactivity, high cell adhesion, adjustable biodegradation rate and good osteoconduction.[19] It is used as filler in ionomer cements to fill carious lesions or as a colloidal suspension in toothpastes, chewing gums or mouthwashes to promote remineralization of carious lesions and/or to prevent tooth demineralization.[20]

As a postulated precursor in the formation of biological hydroxyapatite, ACP has also been evaluated as a filler phase in bioactive polymeric composites.[17] Hydroxyapatite is now considered as an adequate alternative to autografts and allografts (ISO 13175-3:2012). The synthetic origin of these devices guarantees that no transmittable disease will contaminate the patient. The biocompatibility and safety of hydroxyapatite, β-tricalcium phosphate and calcium phosphates is well established within the literature.[21]

Henceforth, hydroxyapatite is biologically safe or in other terms biocompatible to be used in the oral cavity as a desensitization and remineralization material.

The application of calcium phosphates in oral care has become of interest in the last decade or so with more insight into remineralisation in dental tissues. Hydroxyapatite, β-tricalcium phosphate, amorphous calcium phosphate (ACP), calcium glycerophosphate, and calcium phosphosilicate are some examples of calcium phosphates used in oral care mainly as components of dentrifices or mouthwashes.

Calcium phosphate compositions for use as erodible materials in the present invention comprise one or more calcium phosphates. Calcium phosphate, as used herein, is the family of substances containing calcium ions together with phosphates, metaphosphates or pyrophosphates and mixtures thereof. In addition, the substances may contain hydrogen, strontium, fluoride, carbonate, nitrate, ammonium, magnesium, zinc, titanium, tin, silver and hydroxide ions.

The properties of the calcium phosphate composition can be tailored to provide the required rate of erosion (dissolution) in the type of acid to be studied. Particular parameters which can be varied include the form(s) of calcium phosphate present in the composition, the calcium:phosphate ratio, the density and surface roughness of the composition, as well as the thickness of the layer(s) in the device.

The calcium phosphate composition may optionally comprise a binder.

The binder, if present, in the calcium phosphate composition is useful for maintaining the calcium phosphate particles in a stable layer. Preferably, the binder is acid soluble, stable in thin cross-section and/or biocompatible.

Examples of binders suitable for use in the calcium phosphate composition include, but are not limited to, polycaprolactone (PCL), polylactic acid (PLA), polyglycolic acid (PGA) and co-polymers (PLGA), polyvinyl alcohol (PVA), proteins such as collagen or gelatine, alginic acid, plaster of paris ($CaSO_4$), and methacrylate binders. A polylactic acid may be poly-L-lactic acid (PLLA), poly-D-lactic acid (PDLA) or a mixture thereof. Examples of methacrylates commonly used in dental applications include methyl methacrylate and hydroxyethyl methacrylates.

In one embodiment, the binder also comprises an adhesive. Devices in which the binder comprises an adhesive may have self-adhesive properties. For example, such devices could be affixed to the surface of a tooth without the need for an additional adhesive. For example, a methacrylate binder could also serve as an adhesive for bonding the device to the tooth surface.

Types of Calcium Phosphate

Many forms of calcium phosphate are known per se and can be used in the present invention. Examples of calcium phosphate include, but are not limited to, monocalcium phosphate ($Ca(H_2PO_4)_2$), dicalcium phosphate ($CaHPO_4$, also known as dibasic calcium phosphate), tricalcium phosphate ($Ca_3(PO_4)_2$, also known as tribasic calcium phosphate or tricalcic phosphate), hydroxyapatite ($Ca_5(PO_4)_3(OH)$), apatite (including hydroxyapatite, fluorapatite, chlorapatite, $Ca_{10}(PO_4)_6(OH, F, Cl)_2$, magnesium-substituted apatite, strontium-substituted apatite, titanium-substituted apatite, tin-substituted apatite, silver-substituted apatite, carbonate-substituted apatite, fluoride substituted apatite and mixtures thereof), octacalcium phosphate ($Ca_8H_2(PO_4)_6$), and tetracalcium phosphate ($Ca_4(PO_4)_2O$), and mixtures thereof.

Crystalline forms of the different types of calcium phosphate are known per se. The calcium phosphate may be in an anhydrous form or may be in a hydrate crystalline form, such as a hemihydrate, monohydrate, dihydrate, trihydrate, tetrahydrate, or pentahydrate. For example, monocalcium phosphate may be anhydrous or in the form of monohydrate (or mixtures thereof). Dicalcium phosphate may be dihydrate, a hemihydrate or anhydrous forms (or mixtures thereof). Octacalcium phosphate may, for example, be in the pentahydrate form.

The calcium phosphate crystalline form may be in a particular crystalline phase. For example, a tricalcium phosphate may be α-tricalcium phosphate, α'-tricalcium phosphate, or β-tricalcium phosphate.

Particular examples of calcium phosphate useful in the present invention include monocalcium phosphate monohydrate (MCPM), dicalcium phosphate (DCPA), dicalcium phosphate dihydrate (DCPD), octacalcium phosphate (OCP), precipitated hydroxyapatite (PHA), precipitated amorphous calcium phosphate (ACP), monocalcium phosphate (MCP), α-tricalcium phosphate (α-TCP), β-tricalcium phosphate (β-TCP), sintered hydroxyapatite (SHA), oxyapatite (OXA) and mixtures thereof.

In some embodiments, the calcium phosphate contains ionic substitutions. In some embodiments, the calcium phosphate contains metallic substitutions, preferably selected from a substitution of calcium with a metal selected from magnesium, strontium, titanium, tin, silver and mixtures thereof, more preferably, the metal is selected from magnesium and tin.

In some embodiments, the calcium phosphate contains non-metallic substitutions, preferably selected from carbonate and fluoride, more preferably carbonate. These could also be polymers such as carboxylic acids, phosphonic acids, hyaluronic acid, chitosan or dextran.

In some embodiments, the calcium phosphate contains metallic and non-metallic substitutions which modifies their resistance to acids and allows for increased resolution of acid-specific effects. This includes increased dissolution and reprecipitation rates. The dopant ions may also serve as colour indicators in their own right and may provide anti-fouling properties to the device (e.g. through the well-described effect of Ag+ ions).

Calcium phosphates useful in the devices of the present invention may include hydroxyapatites, including Sr/F—/Ti/Ag substituted hydroxyapatites, (alpha/beta) tri- and monocalcium phosphates.

In some embodiments, the calcium phosphate composition comprises β-TCP.

In some embodiments, the calcium phosphate composition comprises a mixture of β-TCP and monocalcium phosphate.

Calcium to Phosphate Ratio

The calcium to phosphate (Ca:P) ratio can be defined as the ratio of the number of calcium ions to the number of phosphate ions in the empirical formula of the calcium phosphate. For example, the Ca:P ratios of a number of calcium phosphates are shown in the below table.

| Compound | Formula | Ca:P |
|---|---|---|
| monocalcium phosphate monohydrate | $Ca(H_2PO_4)_2 \cdot H_2O$ | 0.5 |
| monocalcium phosphate anhydrous | $Ca(H_2PO_4)_2$ | 0.5 |
| dicalcium phosphate anhydrous | $CaHPO_4$ | 1.0 |
| dicalcium phosphate dihydrate | $CaHPO_4 \cdot 2H_2O$ | 1.0 |
| octacalcium phosphate | $Ca_8H_2(PO_4)_6 \cdot 5H_2O$ | 1.33 |
| α-tricalcium phosphate | $\alpha\text{-}Ca_3(PO_4)_2$ | 1.5 |
| β-tricalcium phosphate | $\beta\text{-}Ca_3(PO_4)_2$ | 1.5 |
| hydroxyapatite | $Ca_5(PO_4)_3OH$ | 1.67 |
| fluorapatite | $Ca_5(PO_4)_3F$ | 1.67 |
| tetracalcium phosphate | $Ca_4(PO_4)_2O$ | 2.0 |

The calcium phosphate compositions used in the devices of the invention preferably contain calcium and phosphate ions in an overall ratio of less than 1.67:1.

In some embodiments the calcium phosphate composition contains calcium and phosphate ions from a single calcium phosphate which has a calcium to phosphate ratio of less than 1.67:1.

In some embodiments the calcium phosphate composition contains more than one type of calcium phosphate wherein the bulk calcium to phosphate ratio is less than 1.67:1, in theory such an embodiment could comprise amounts of calcium phosphate with a calcium to phosphate ratio of greater than 1.67:1.

Calcium Phosphate Particle Size

The calcium phosphates within the calcium phosphate composition are typically provided as small particles. The particles of calcium phosphate preferably have a mean particle diameter in the tenth and ninetieth percentile range within 2 μm to 100 μm, as confirmed by high resolution scanning electron microscopy. Without wishing to be bound by theory, nanoparticles or particles smaller than about 2 μm may have biocompatibility issues whereas particles greater than about 100 μm may be more susceptible to abrasion rather than erosion, and so would be less preferred. In some embodiments the composition may be a hybrid of smaller particle diameter and larger particle diameter.

In some embodiments, the calcium phosphate particles may have a mean particle diameter between about 2 μm and about 100 μm. In some embodiments, the calcium phosphate particles may have a mean particle diameter between about 2 μm and about 50 μm. In some embodiments, the calcium phosphate particles may have a mean particle diameter between about 2 μm and about 20 μm. In some embodiments, the calcium phosphate particles may have a mean particle diameter between about 4 μm and about 15 μm.

The measurement of mean particle size is preferably achieved using high resolution scanning electron microscopy, which is highly reproducible. Other commonly used particle size analysers are based e.g. on light diffraction or size exclusion methodologies. In a sintered material, the particle size may be determined prior to sintering.

Calcium Phosphate Composition Density

The mean density of the calcium phosphate composition in the erodible layers is preferably less than 3.18 g/mm³ but greater than 1.20 g/mm³, as determined by dividing the weight of the composition in grams by the volume.

Without wishing to be bound by theory, a density in this range means that the composition is expected to be less dense than hydroxyapatite but of greater density than water or PMA.

In some embodiments, the density may be between 1.2 g/mm³ and 3.18 g/mm³. In some embodiments, the density may be between 1.20 g/mm³ and 2.84 g/mm³. In some embodiments, the density may be between 1.20 g/mm³ and 2.50 g/mm³. In some embodiments, the density may be between 1.50 g/mm³ and 2.50 g/mm³.

Indicator

The device of the invention comprises an indicator in at least one layer. The indicators in the device of the invention provide a response upon erosion which indicates the presence of acid.

In some embodiments, the indicator is a separate composition and/or is provided in a separate indicator layer. In other embodiments, a separate indicator may not be required, for example the erodible layer may itself serve as the indicator by producing a visible change (in particular a colour change) as a result of its erosion/dissolution.

In one embodiment the indicator enhances contrast between eroded and non-eroded devices thereby giving a visual determination of whether or not erosion has taken place.

For example, a layer containing an indicator is covered by a layer which does not contain an indicator (e.g a white or tooth coloured layer) in a non-eroded device. Upon erosion of the covering layer, in use, the indicator containing layer is exposed, as indicated by a change in visible colour, imparted by the indicator.

Alternatively, the initially exposed layer may contain an indicator, thereby imparting a colour when the device is first affixed in the mouth of a subject. Loss of the indicator layer in this embodiment causes loss of the colour and thereby indicates erosion of the device.

Alternatively, erosion/dissolution of the erodible material produces a visible change (for example, a colour change) in the erodible layer, which indicates that said erosion/dissolution has taken place.

The visual contrast can be achieved, for example, by the dispersion of an indicator throughout a given layer or set of layers. In such embodiments, any additive capable of imparting a colour or other visual cue to the layer through which is it dispersed is suitable as an indicator. In the case of fluorescent indicators, the visual contrast may only be discernible under a source of electromagnetic radiation (such as ultraviolet light).

Indicators are preferably dispersed uniformly throughout the relevant layers.

Indicators include, but are not limited to dyes, pigments (including fluorescent dye and pigments), opacifiers, fluorescently labelled beads, and combinations thereof. For example, commercially available indicator dyes suitable for intraoral use may be used as colour indicators.

In some embodiments, suitable indicators may be comprised of sparingly soluble or insoluble particles of one or more pigments including, but not limited to: Tartrazine—

E102; Quinoline Yellow—E104; Sunset Yellow—E110; Carmoisine—E122; Ponceau 4R—E124; Allura Red—E129; Indigotine—E132; Brilliant Blue FCF—E133; Patent Blue V—E131; Brilliant Black PN—E151; Chocolate Brown HT—E155. In some embodiments, tartrazine (E102), quinoline yellow (E104), or patent blue V may be used.

In a multilayer device each layer may contain a different indicator. In such an example, different extents of erosion of the device would result in the exposure of a different indicator: this would be useful in the determination of the rate of erosion. Alternatively, a single indicator could be dispersed uniformly in each layer at a different concentration, such that a different intensity of colour can be observed in each subsequent layer. For example, towards the top layer (i.e. farthest from the surface of the tooth to which the device is affixed when in use) a lower concentration of indicator could be used and the concentration could increase sequentially or in a graded manner through to the base layer (i.e. that which is closest to the surface of the tooth to which the device is affixed when in use), in this regime, greater erosion would lead to a more intense colouration. Such a gradation of colours could also be reversed, for example a high concentration of indicator near the top layer and a lower concentration near the base layer.

In some embodiments, at least one erodible (e.g. calcium phosphate) layer contains an indicator.

In some embodiments a separate indicator layer, which may be non-erodible, is present, for example as the bottom layer of the device. In this case, the indicator may be dispersed in a resin-based layer. Other possible matrices for such a layer include, but are not limited to: methacrylate, gelatine, casein, collagen, zirconia, titanium, stainless steel, gold, glass ionomer cement (a commonly used cement in dentistry).

Layers

The devices of the invention preferably have a layered structure. The number of layers and the thickness of the layer(s), may vary as needed.

The devices of the invention comprise at least one erodible layer and at least one indicator. The indicator(s) may be in a separate indicator layer and/or within an erodible layer. The erodible layer may also itself act as the indicator (i.e. where erosion of the erodible layer inherently produces a visual change).

Number of Layers

Preferably, the device of the invention is, or comprises, a multi-layered system. However, it may comprise a single erodible layer which also comprises the indicator (i.e. which also serves as an indicator layer).

Accordingly, in one embodiment, the device comprises a single layer of an erodible material, which also comprises an indicator. Loss of the indicator signal signifies the loss of the single layer of the device due to the presence of acid.

In another embodiment, the device comprises two layers. The bottom layer, which, in use, is closest to the device surface which is affixed to the tooth, comprises the indicator. The top layer, which, in use, is farthest from the device surface which is affixed to the tooth, is an erodible layer. Preferably this layer is white or tooth-coloured and preferably contains no indicator. In some embodiments, this layer comprises an erodible material, which may for example be a calcium phosphate composition.

In another embodiment, the device comprises n layers. The top layer, which, in use, is farthest from the device surface which is affixed to the tooth, preferably comprises an erodible material and no indicator. The remaining n−1 layers include the bottom layer, which, in use, is closest to the device surface which is affixed to the tooth, and all layers between the bottom and top layers. It is possible for the n−1 layers to all comprise an indicator. Alternatively, some of the n−1 layers comprise an indicator and are interspersed with erodible layers which do not comprise an indicator.

Where there are two or more indicator-containing layers, said indicator-containing layers may be arranged to form a colour gradient or produce distinct colours The utility of having a colour gradient throughout the device or a set of distinctly coloured layers is to allow the determination of the extent of erosion of the device. For example, through comparison with a colour chart, the number of layers which have been eroded (or dissolved) can be determined and hence the severity of the acid erosion assessed.

Thickness of Layers

The erodible layer(s) in the devices of the invention may vary in thickness. The thickness of the layers will affect the rate at which the layer is eroded, as will be understood by the person skilled in the art, and hence the rate at which an underlying indicator layer is exposed. The thickness of the layer can be controlled during manufacture to ensure a consistent thickness.

In some embodiments, each erodible layer preferably has a thickness of between 100 μm and 1500 μm.

Where a separate indicator layer is present, which is not also an erodible layer, this layer preferably has a thickness of between 25 μm and 50 μm In some embodiments, the total thickness of all of the erodible layers in the device is preferably in the range of 100 μm to 1500 μm.

Other Features of the Device

Bracket

In some embodiments, the device is housed within a bracket. Preferably, the bracket is pre-formed from a resin-based matrix material, such as commonly used for orthodontic brackets. This material will be biocompatible, compatible with adhesives, non-traumatic and serves to protect the indicators from the mechanical component of wear as shown above.

The bracket is readily applicable to a tooth surface, and can be fixed to the surface for example by means of a dental adhesive.

The bracket may be reversibly bonded to the tooth using dental adhesives (such as hydroxyethyl methacrylate or polyethylene). Alternatively, the device may be directly and reversibly bonded to the tooth using the same methyacrylate or polyethylene-based adhesives.

Adhesive

In some embodiments, the device comprises an adhesive for fixation of the device to a tooth surface.

Adhesives suitable to fix the device to a tooth in the oral cavity of a subject are generally known in the art. Examples include, but are not limited to, universal adhesives, total etch adhesives and self-etch adhesives, based on methacrylates, such as hydroxyethyl methacrylate.

The adhesive may be applied to a surface (i.e. the bottom surface) of the device.

In some embodiments, the adhesive may be applied to a bracket containing the device.

In some embodiments, the adhesive may be included in one or more of the layers of the device (i.e. in an erodible layer or in a separate indicator layer). In these embodiments the device is self-adhesive i.e. no separate adhesive need be applied in order to fix the device to a tooth.

Size and Shape

The device of the invention is intended for application to a surface of a tooth within the oral cavity of a subject and is therefore preferably sized appropriately, so as to fit onto the surface of a single tooth.

In preferred embodiments, the entire device ranges from 2 mm to 4 mm in width and length and from 0.5 to 2 mm in depth.

The shape of the device is not particularly limited. In some embodiments, the surface of the device is substantially flat. In other embodiments, a domed shape may be preferred.

Manufacture of the Device

Additive manufacturing, also known as 3D printing, has emerged over the past 3 decades as a disruptive technology for rapid prototyping and manufacturing and has found widespread application, for example, in manufacturing layered calcium phosphates [15]. Binding agents such as poly vinyl alcohol are either left in situ or removed through a sintering process at high temperatures, leading to fusion of calcium phosphate particles and thermal decomposition of the binding agent.

In some embodiments, the erodible layers in the devices of the invention are manufactured using 3D printing techniques.

In some embodiments, in particular embodiments comprising calcium phosphate and indicator layers, the layers may be deposited via chemical deposition techniques, which are known in the art, optionally followed by sintering (which may comprise sintering of the components or bulk, after assembly of the layers).

The device itself may be 3D printed or milled according to the required composition type. The indicators may either be printed as one material or in layers with assembly after printing. The device may then be sintered as required.

Following device construction it may be bonded within a pre-formed composite resin housing with the outermost layer exposed to the environment.

Methods of Detection and Diagnosis

The devices of the invention are useful for the detection of elevated acid levels within the oral cavity and for the early detection of pathological tooth erosion. The devices of the invention may also be useful to differentiate the type(s) of acid present (i.e. mineral/gastric acid or organic/dietary acid). Detection of acid, in particular hydrochloric acid, in the oral cavity may be indicative of certain gastric disorders and the devices of the invention are therefore also useful in methods of diagnosis of those disorders.

The invention accordingly provides methods of detecting the presence of acid (for example, gastric and/or dietary acid) within the oral cavity and methods of diagnosing a disease or condition characterised by pathological erosive tooth wear and/or characterised by the presence of acid within the oral cavity. In some embodiments, the methods involve differentiating the type of acid present.

In some embodiments, the invention provides a method of detecting acid in the oral cavity and/or of detecting pathological tooth erosion, comprising the steps of:

a) applying an oral acid-sensing device as described herein to a tooth surface within the oral cavity of a subject; and b) monitoring the device, over a suitable time period, to determine the response from the indicator.

This method may also includes the steps of:

c) determining the presence or absence of acid in the oral cavity; and/or d) determining the presence or absence of pathological tooth erosion.

In some embodiments, the invention provides a method of diagnosing a disease or condition characterised by pathological erosive tooth wear and/or characterised by the presence of acid within the oral cavity, said method comprising the steps of:

a) applying an oral acid-sensing device as described herein to a tooth surface within the oral cavity of a subject; and b) monitoring the device, over a suitable time period, to determine the response from the indicator.

This method also includes the steps of:

c) determining the presence or absence of acid in the oral cavity; and/or d) determining the presence or absence of pathological tooth erosion; and/or e) determining the presence or absence of said disease or condition.

In some embodiments of the above methods, the acid is or comprises mineral acid.

In some embodiments, the acid is or comprises gastric acid, for example hydrochloric acid.

In some embodiments, the acid is or comprises dietary acid, for example an organic acid such as citric acid.

Application of the Device

Fixation of the device to the tooth surface can be achieved using standard dental adhesives, as are well known in the art. Adhesives suitable for use with the devices of the invention are further described above.

Application of the device to the tooth may be performed, for example, by a dental professional using standard techniques. Alternatively, if a suitable adhesive is used or in the case of a self-adhesive device, the device may be applied to the tooth surface by someone other than a dental professional, such as another healthcare professional or even by the subject themselves.

In some embodiments, the device is preferably fixed to a non-visible tooth surface i.e. to the rear (palatal) surface of a front tooth, or to a back tooth. This is to prevent wearing of the device from affecting the appearance of the subject.

Monitoring

The device remains in place on the tooth surface over a suitable test period. At the end of a test period and/or regularly throughout a test period, the device is visually inspected to determine whether there is any response from the indicator.

A suitable test period can be determined depending on relevant factors such as the properties of the device used and the likely acid(s) to be detected.

In one embodiment, the time period is between 4 h and 28 days. In one embodiment, the period is between 12 h and 28 days. In one embodiment the period is between 1 and 7 days. In one embodiment the period is between 2 and 4 days. In one embodiment the period is 3 days. In one embodiment, the period is between 24 h and 72 h.

In some embodiments, a food diary of the subject is kept for the duration of the test period.

Indicator Response

In the methods of the invention, a positive detection result is obtained when the indicator in the device provides a positive response i.e. a visual indication that erosion has occurred.

As described in detail above, such a response may comprise appearance of colour from an indicator-containing layer beneath an erodible layer. In other embodiments, the response may involve disappearance of colour from an erodible indicator-containing layer.

Diseases/Conditions

The methods of the invention may be useful for the detection and diagnosis of any disorder, disease or condition which is characterised by the presence of elevated levels of acid in the oral cavity. The methods of the invention are particularly useful for the diagnosis of conditions characterised by the presence of mineral acids, in particular hydrochloric acid, in the oral cavity.

In some embodiments the disease or condition is selected from gastro-oesophageal reflux disease, extra-oesophageal reflux disease, chronic cough, chronic obstructive pulmonary disease, severe asthma, bulimia, and erosive tooth wear.

In some embodiments, the disease or condition is gastro-oesophageal reflux disease or extra-oesophageal reflux disease.

In some embodiments, the disease or condition is gastro-oesophageal reflux disease.

In some embodiments the disease or condition is erosive tooth wear.

Other Features of the Methods

The devices and methods of the invention will allow any health care professional to assess for extra-oesophageal reflux within a short diagnostic window. For the first time, primary care professionals will be able to categorise the risk based upon the patient's chemical, biological and behavioural risk factors, improving the decision making process for complex treatment plans.

This innovation provides, for the first time, an accurate method of extra-oesophageal testing which will be non-invasive, cheap and highly selective. There is currently no other approach in use within primary, secondary or tertiary care that can determine disease activity and indicate the source of the acid damage. This will result in more timely referrals for medical investigations and patient empowerment to monitor and control their own disease progression.

In addition, the methods and devices of the invention could be used to establish the effectiveness and minimal effective dose needed for proton pump inhibitors. These drugs are prescribed for long term use and have multiple side effects. The prescription of proton pump inhibitors is currently determined by symptoms which we know are a poor marker of gastro-oesophageal reflux disease [2]. By using the devices and methods of the invention, a GP could gauge the minimum effective dose for proton pump inhibitors or reassess the need for prescription or referral effectively within a short time period.

GENERAL REMARKS

Ambient temperature as used herein has its normal meaning, namely at a temperature of the surrounding atmosphere. Ambient temperature is typically in the region of 0 to 40° C.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/− 10%.

EXAMPLES

The examples below are illustrative of particular embodiments and should not be construed as limiting the invention in any way.

Exemplary devices prepared by the present inventors have used indicator layers, containing differentially labelled (fluorescently) latex beads, or dyes, or insoluble pigments, held within a resin sub-structure which was coated in an erodible layer composed of a 99.5% w/v calcium phosphate particulate phase, tailored to the type of acid exposure to be studied. In the case of short term exposures, where overall acid experience or differentiating between mineral acid/organic acids (i.e. stomach acid HCl or dietary acid such as citric acid) is desired, the choice of calcium phosphate rests between full apatites (such as fluorapatite/hydroxyapatite) or a more readily soluble CaP, such as beta-TCP.

In pilot studies, by varying the thickness of the covering CaP layer, the inventors were able to determine the type of acid experience, i.e. HCl or citric acid, after the equivalent of 10 minutes exposure. This could be used to clearly differentiate between GORD/reflux or dietary acids.

After said exposure, a bright red and yellow (HCl) or yellow only (weaker acids) indicator layer underneath the CaP (that now was dissolved) is revealed.

Figure 3:
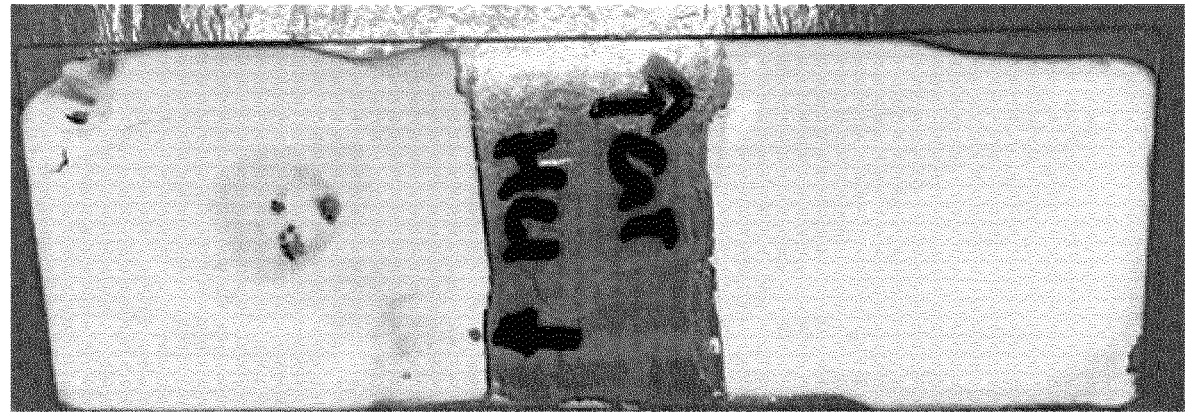
FIG. 3: Calcium phosphate material following dropwise erosion assay. The lesion on the left is caused by HCl exposure. The lesion on the right is caused by citric acid exposure.

In order to demonstrate the ability to tailor the crystalline CaP phase to differentiate between (dietary) citric acid or intrinsic (hydrochloric) acid at physiological levels, prototypes were made using beta tricalcium phosphate bonded to an reporter layer containing biocompatible dental adhesives. A consistent thickness of 1 mm (+/−0.1) mm was generated and a dropwise erosion assay carried out for 30 minutes after which the slides were washed and dried, prior to 3D scanning (see FIG. 3).

Figure 4:
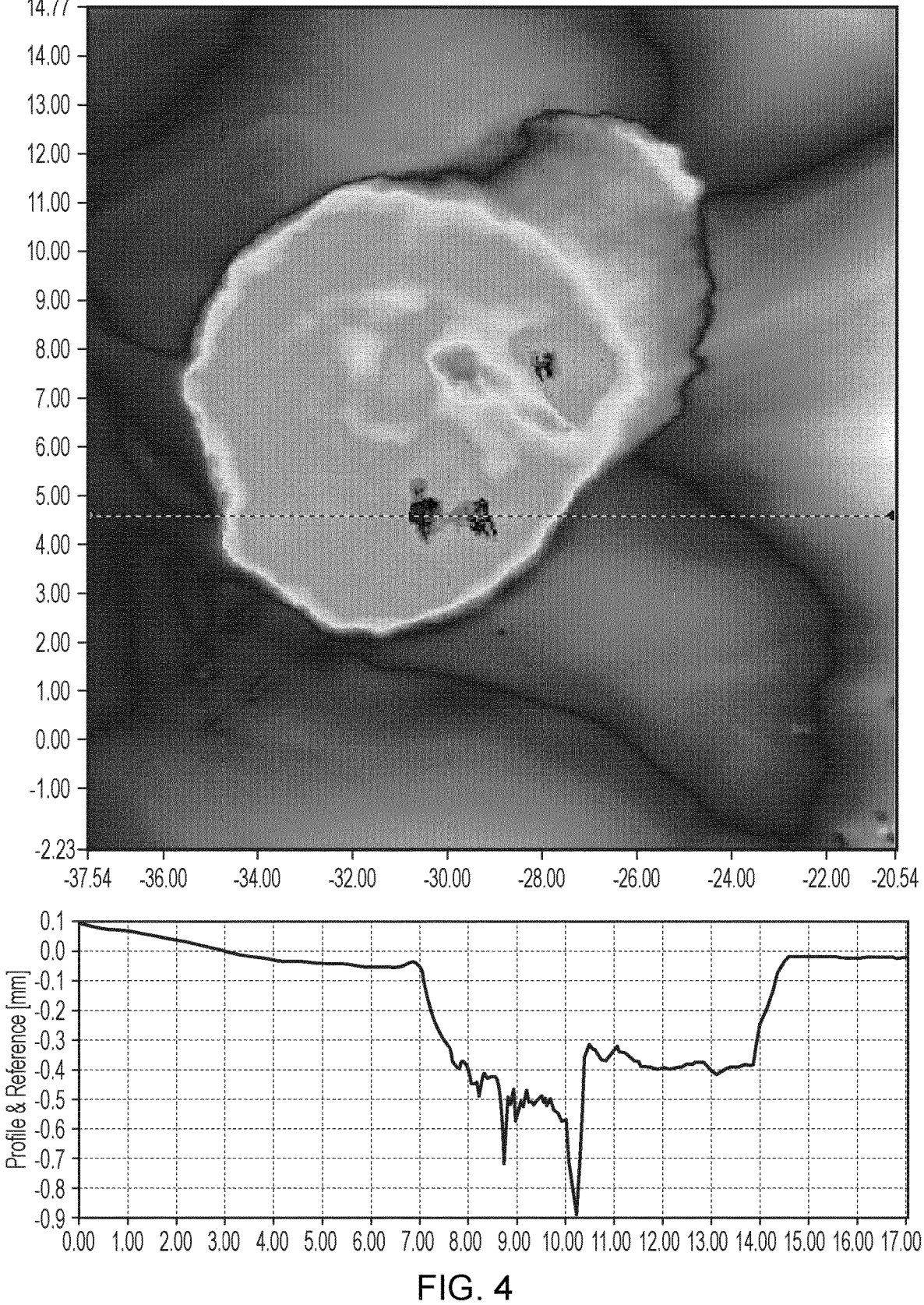
FIG. 4: Cross sectional image through HCL lesion.
Figure 5:
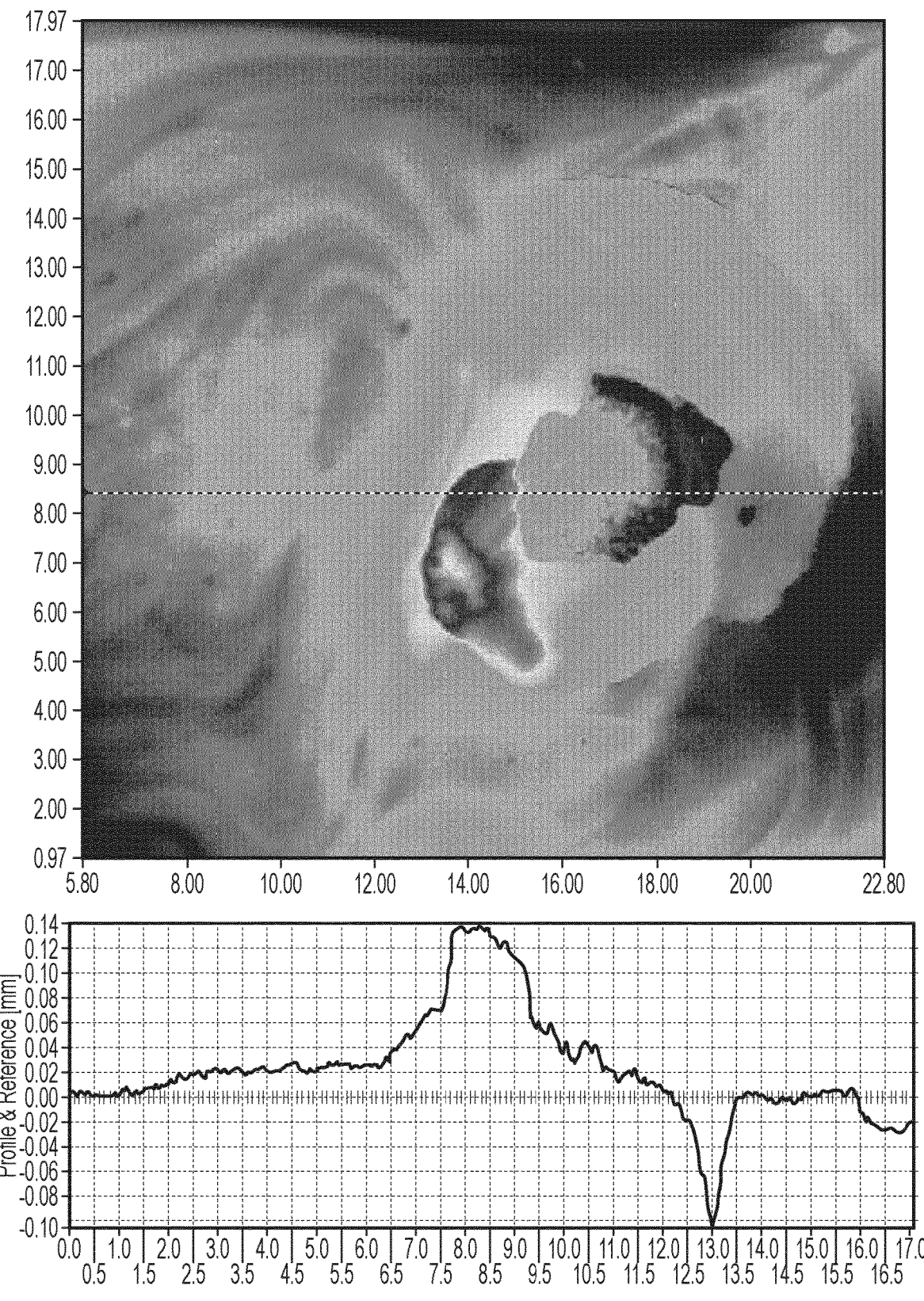
FIG. 5: Cross sectional image through citric acid lesion.
Figure 6:
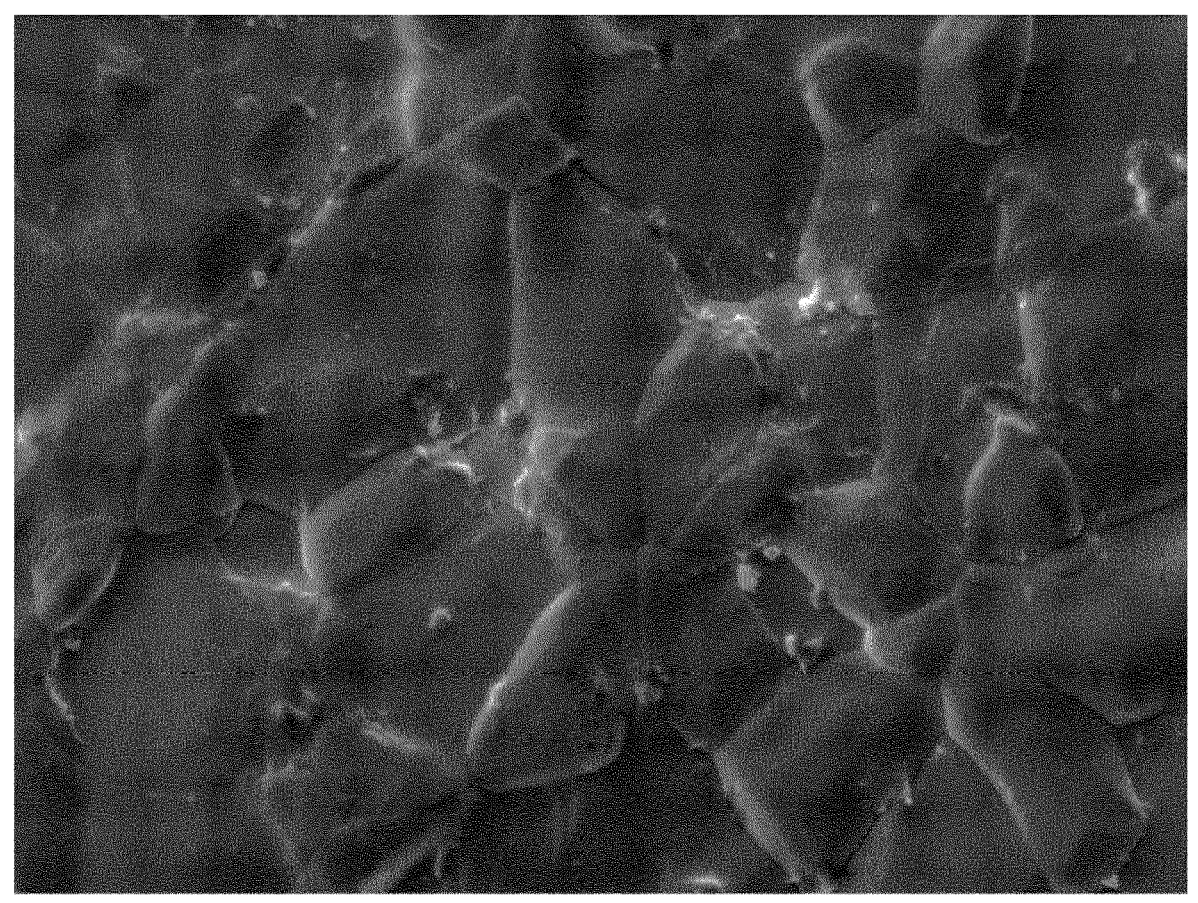
FIG. 6: SEM image of a β-TCP layer before erosion with citric acid

FIGS. 4 and 5 illustrate profilometric images of the material under different acid conditions. FIG. 4, top, shows a laser profilometric image of the nanohydroxyapatite exposed to 0.1M HCL for 10 minutes. The rough size of the lesion was 11.4 mm×11 mm. The maximum profile depth was 0.9 mm (FIG. 4, bottom). FIG. 5, top, shows a laser profilometric image of the nanohydroxyapatite exposed to 0.3% citric acid for 30 minutes. The rough size of the lesion was 6.9 mm×7 mm. The maximum profile depth was 0.16 mm. There was deposition and crystal remineralisation when citric acid was applied to the nanohydroxyapatite (FIG. 5, bottom).

A number of calcium phosphates have been examined including dicalcium phosphate, MCP, DCP, HA and alpha/beta TCP. The binder in these examples was comprised of an acid soluble phase, such as PLLA (poly-l-lactic acid) or standard methacrylate-based binders to provide hydrophobic interactions with the base indicator layer.

Commercially available indicator dyes suitable for intraoral use are used as colour indicators.

The proposed clinical embodiment comprises a composite resin housing, similar but smaller to an orthodontic bracket which can be applied to the dental surface using conventional dental bonding techniques. Similar to tooth jewels, no phosphoric acid etch will be used to enable post-exposure removal and ensure no residue will remain on the tooth.

The device itself is 3D printed or milled according to the required composition type. The indicators are either printed as one material, or in layers with assembly after printing. The device is then sintered as required. Following device construction, it is bonded within a pre-formed composite resin embodiment with the outermost layer exposed to the environment.

A particular utility of the devices of the invention is the diagnosis of underlying pathological conditions associated with the presence of intraoral acids. A small device can be applied, for example with a small plastic disposable placement device, on the back of a non-visible tooth surface by any professional. The test will give a colour read out after three days and can then be removed by applying light pressure with a small plastic removal device. For the first time, primary care professionals will have a clear indication of whether gastric acid is reaching the oral cavity. This will facilitate earlier medical intervention, screening and further medical examination (e.g. gastroscopy).

A further use will be to allow screening, risk profiling and monitoring of erosive tooth wear progression. If there is doubt whether a patient's diet and/or underlying disease is causing tooth wear, a device according to the present invention can be applied and feedback provided. This can aid as a patient information tool, establishing individual risk and could be used as a method of reinforcing dietary advice or empowering the patient to take control over their own disease process, thus avoiding costly treatment.

Figure 7:
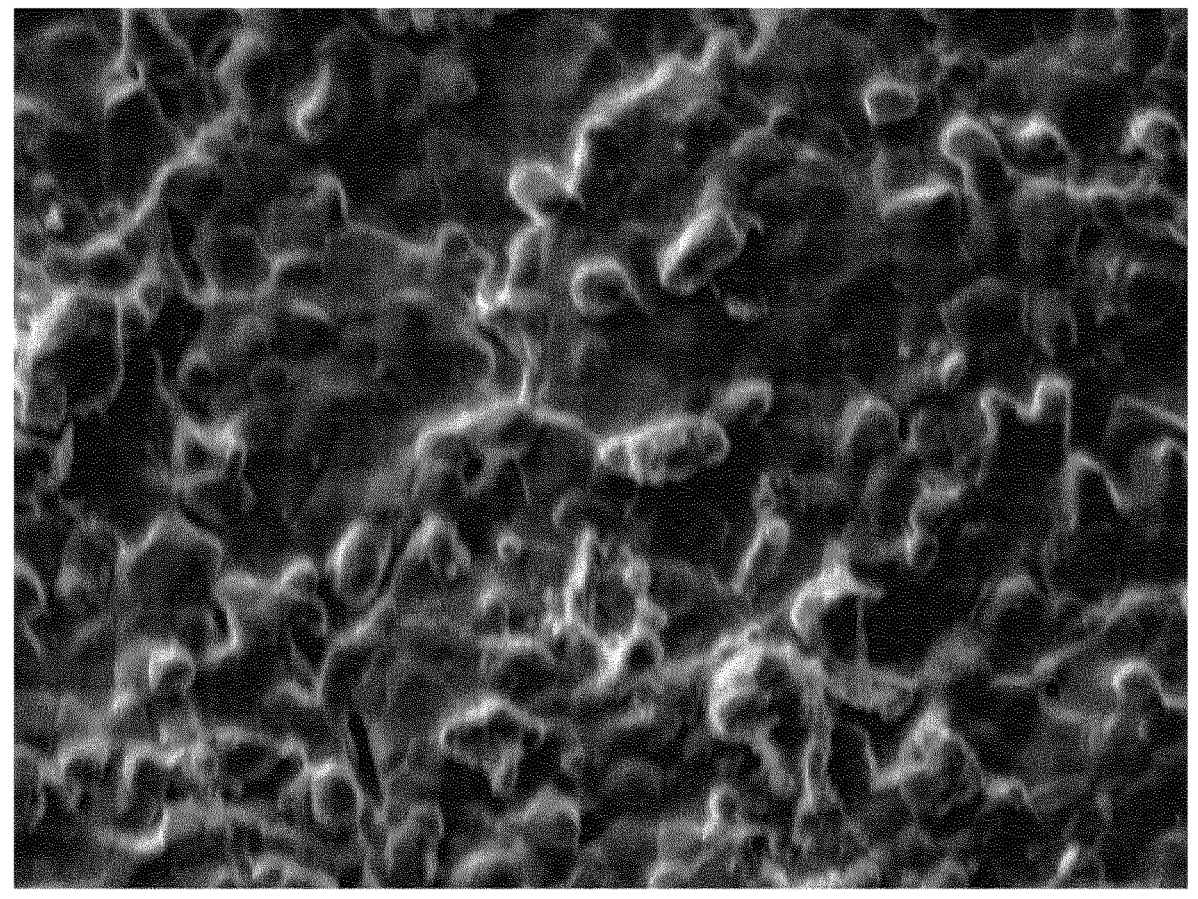
FIG. 7: SEM images of a β-TCP layer after erosion with citric acid

Example 1—Comparing the Rate of Profilometric Loss and Surface Roughness Changes of Natural Enamel, HA and β-TCP Natural human molar samples (n=20) were collected (REC ref 12/LO/1836) and the buccal surfaces sectioned using a water-cooled diamond wafering blade (XL 12205, Benetec Ltd., London, UK) at a speed of 300 rpm and force of 150 g. Fully dense crystalline calcium phosphate discs of hydroxyapatite (HA) (blue, 12×2 mm, Plasma Biotal Limited, Derbyshire, UK) and beta-tricalcium phosphate (β-TCP) (white, 10×2 mm, Plasma Biotal Limited, Derbyshire, UK) were also sectioned into four pieces creating twenty 3 mm wide samples of each material. The enamel, HA and β-TCP quarter pieces were placed into custom-made silicone moulds (size 5 mm×2.5 mm×2 mm) and embedded in self-curing acrylic repair material (liquid and powder (cadmium free), Oracryl, Bracon, East Sussex, UK) leaving the outer surface exposed. HA and β-TCP samples were polished using successively finer silicon-carbide discs (Versocit, Struers A/S, Copenhagen, Denmark) of grit 500, 1200 and 2000 for 5 seconds, 25 seconds and 90 seconds respectively, using a water-cooled rotating polishing machine at 150 rpm and 10N constant pressure (LaboPol-30, Struers ApS, Ballerup, Denmark). This resulted in the surface being smooth and polished with a flatness tolerance ±1 μm. Adhesive tape was placed on the samples as seen in FIG. 7, right, to leave an exposed surface approximately 1 mm×3 mm wide with two unexposed reference areas on either side. Specimens were stored in dry conditions prior to the acid exposure cycling.

Citric acid solution was prepared at 0.3% (0.016M). This solution gave a pH of 2.67±0.1. For the HCl, a stock 1M Glycine-HCl Buffer, pH 2.7±0.1 (Polysciences, Inc., Warrington, PA) was used. Each of the groups of natural enamel surfaces (n=20), fully dense HA discs (n=20) and fully dense β-TCP discs (n=20) were randomly divided into two subgroups to be exposed to either citric acid (n=10) or HCl/glycine (n=10) at pH 2.67. Samples were mounted in custom acrylic holders, placed in plastic trays (330 ml, 105 mm×105 mm×25 mm) and exposed to 80 ml of either citric acid or HCl/glycine buffer under agitation using an orbital shaker at 60 rpm (Stuart Orbital Shake SS1, Bibby Scientific Limited, Staffordshire, UK). Following each acid exposure, the samples were rinsed for 1 minute with deionised water using the orbital shaker at 60 rpm. This was followed by placement in a 100 ml distilled water bath, samples here were left, unstirred for 60 minutes. This experimental cycle was repeated three times giving a total exposure time of 30 minutes. The experiment was carried out at room temperature. After the experiment, samples were left to air-dry for 12 hours at room temperature and the adhesive tapes were carefully removed.

Figure 8:
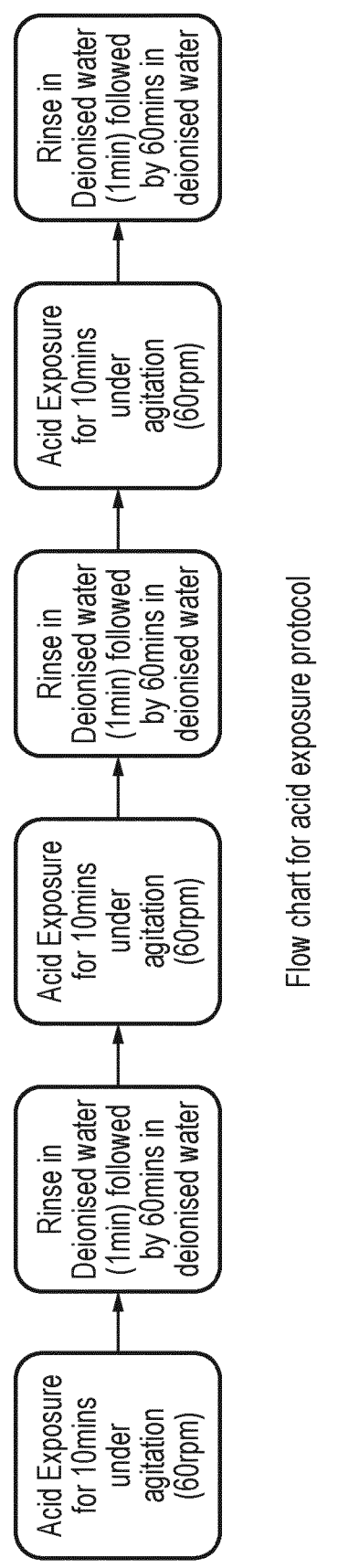
FIG. 8: Flow chart for acid exposure protocol

The step heights of the samples were measured using a white light non-contacting laser profilometer (XYRIS 2000; Taicaan, Southampton, UK) with a spot size of 7 μm and a resolution of 0.01 μm. A 3×1 mm area of the sample was scanned to ensure areas of the reference and the eroded area were captured enabling the step height to be measured. The sample was scanned in a raster pattern which took measurements every 10 μm in the X and Y direction meaning 301 by 101 data points were taken. Data were analysed using Boddies v1.92 (Taicaan, UK), the light grey areas are the reference areas whilst the dark grey area in the centre is the eroded area as seen in FIG. 8.

The step height was calculated by measuring the depth of the affected area on the sample which was from the reference area to the midpoint of the trough. Five measurements were made per sample at different points and the average of these measurements was calculated to assess the mean profilometric loss in microns (μm) per sample. The Sa (arithmetical mean height) roughness change was also determined using the Boddies software after applying a gaussian filter of 0.025 μm.

Samples were analysed using SEM-EDS. A SUPRA 35 VP field emission SEM instrument combined with an X-Max EDS instrument (Oxford Instruments, High Wycombe, UK) were used to analyse the particle size and topography of the discs before and after acid erosion.

Data was assessed for normality using Shapiro Wilks test, box plots and histograms in SPSS vers 25 (SPSS Armonk USA). Differences between groups were analysed with a two way ANOVA followed by post-hoc Tukeys analysis. Significance was inferred at $p < 0.05$

The profilometric loss (μm) when natural enamel, HA and β-TCP was exposed to citric acid was 1.50 μm (SD 0.42), 1.42 μm (SD 0.17) and 12.62 μm (SD 1.61) respectively. When natural enamel, HA and β-TCP was exposed following the same protocol to HCl/glycine the profilometric loss was 1.75 μm (SD 0.32), 6.01 μm (SD 0.57) and 30.95 μm (SD 3.06) respectively (graph 1). β-TCP exposure to HCL produced the statistically highest difference.

TABLE 1

Profilometric loss data—all profilometric loss values are given in micrometres (μm). HA—hydroxyapatite; β-TCP—beta tricalcium phosphate. The value in brackets for each table entry is the standard deviation of the measured value

| Calcium phosphate material | Citric acid | HCl/Glycine |
|---|---|---|
| Natural Enamel | 1.50 (0.42) | 1.75 (0.32) |
| HA | 1.42 (0.17) | 6.01 (0.57) |
| β-TCP | 12.62 (1.61) | 30.95 (3.06) |

Acid exposure to natural surfaces produces a smoother surface. In contrast the discs became rougher. The surface roughness (μm) of hydroxyapatite after exposure to citric acid and HCL were 0.33 μm (SD 0.24) and 0.13 μm (SD 0.02). The surface roughness when β-TCP was exposed to the same acids were 0.60 μm (SD 0.09) and 0.82 μm (SD 0.14) respectively with the β-TCP producing a statistically rougher surface. This further increases the surface area for acid exposure.

TABLE 2

Surface roughness—all surface roughness values are given in micrometres (μm). HA—hydroxyapatite; β-TCP—beta tricalcium phosphate. The value in brackets for each table entry is the standard deviation of the measured value

| Calcium phosphate material | Citric acid | HCl/Glycine |
|---|---|---|
| HA | 0.33 (0.24) | 0.13 (0.02) |
| β-TCP | 0.60 (0.09) | 0.82 (0.14) |

TABLE 3

Surface roughness—all surface roughness values are given in micrometres (μm). Natural Enamel is from human tooth samples. HA—hydroxyapatite; β-TCP—beta tricalcium phosphate. The value in brackets for each table entry is the standard deviation of the measured value

| Calcium phosphate material | Citric acid | HCl/Glycine |
|---|---|---|
| Natural Enamel | 0.44 | 0.26 |
| HA | 0.18 | 0.13 |
| β-TCP | 0.60 | 0.82 |

FIGS. 9 and 10 show SEM images of the β-TCP before (FIG. 7) and after (FIG. 8) erosion with citric acid. Remineralisation/citrate deposits can be seen on the surface when β-TCP was exposed to citric acid but not HCL

REFERENCES

A number of publications are cited above in order to more fully describe and disclose the invention and the state of the art to which the invention pertains. Full citations for these references are provided below. The entirety of each of these references is incorporated herein by reference.

[1] H. B. El-Serag, S. Sweet, C. C. Winchester, J. Dent, Update on the epidemiology of gastro-oesophageal reflux disease: a systematic review., Gut. 63 (2014) 871-80.

[2] M. Kaplan, A. Tanoglu, E. Erkul, M. Kara, Y. Yazgan, Association of reflux symptom index scores with gastroesophageal flap valve status, Auris Nasus Larynx. 41 (2014) 543-547.

[3] P. J. F. de Jonge, M. van Blankenstein, W. M. Grady, E. J. Kuipers, Barrett's oesophagus: epidemiology, cancer risk and implications for management., Gut. 63 (2014) 191-202.

[4] V. Tolia, Y. Vandenplas, Systematic review: the extra-oesophageal symptoms of gastro-oesophageal reflux disease in children., Aliment. Pharmacol. Ther. 29 (2009) 258-72.

[5] A. B. Chang, T. J. Lasserson, T. O. Kiljander, F. L. Connor, J. T. Gaffney, L. A. Garske, Systematic review and meta-analysis of randomised controlled trials of gastro-oesophageal reflux interventions for chronic cough associated with gastro-oesophageal reflux., BMJ. 332 (2006) 11-7.

[6] D. Bartlett, A personal perspective and update on erosive tooth wear—10 years on: Part 2—Restorative management, Br. Dent. J. 221 (2016) 167-171.

[7] D. W. Bartlett, D. Evans, A. Anggiansah, B. G. Smith, A study of the association between gastro-oesophageal reflux and palatal dental erosion., Br. Dent. J. 181 (1996) 125-131.

[8] S. O'Toole, M. Pennington, S. Varma, D. W. Bartlett, The treatment need and associated cost of erosive tooth wear rehabilitation—a service evaluation within an NHS dental hospital, BDJ. 224 (2018) 957-961.

[9] S. O'Toole, E. Bernabé R. Moazzez, D. Bartlett, Timing of dietary acid intake and erosive tooth wear: A case-control study, J. Dent. 56 (2017).

[10] Vaesi and Sifrim, Gastroenterology, 154(2) (2018), 289-301

[11] Yadlapati et al. 2015 Abilities of Oropharyngeal pH Tests and Salivary Pepsin Analysis to Discriminate Between Asymptomatic Volunteers and Subjects with Symptoms of Laryngeal Irritation. Clinical Gastroenterology and Hepatology 2015; 14: 535-542

[12] G. Kocak, C. Tuncer and V. Bütün; pH-Responsive polymers; Polym. Chem., 2017, 8, 144

[13] Mylonas et al. 2018 In vitro evaluation of the early erosive lesion in polished and natural human enamel. Dental Materials 2018; 34: 1391-1400

[14] J. M. Rodriguez, R. S. Austin, D. W. Bartlett; In vivo Measurements of Tooth Wear over 12 Months; Caries Res 2012; 46; 9-15

[15] R Trombetta, et al; Annals of Biomedical Engineering, Vol. 45, No. 1, January 2017; pp. 23-44

[16] Legeros, R. Z. (1988). Calcium Phosphate Materials in Restorative Dentistry: a Review. Advances in Dental Research, 2(1), 164-180.

[17] Dorozhkin and Epple (2002); Biological and Medical Significance of Calcium Phosphates; Angew. Chem. Int. Ed.; 41, 3130-3146.

[18] Tamimi F, Kumarasami B, Doillon C, Gbureck U, Le Nihouannen D, Cabarcos E L, Barralet JE. (2008); Brushite-collagen composites for bone regeneration.; Acta Biomater. September; 4(5):1315-21.

[19] P. Feenstra, T & L. De Bruyn, P. (1979). Formation of Calcium Phosphates in Moderately Supersatured Solutions. The Journal of Physical Chemistry. 83.

[20] Combes and Rey (2010); Amorphous calcium phosphates: Synthesis, properties and uses in biomaterials; Acta Biomaterialia; 6; 3362-3378

[21] Daculsi et al., 1999, Biphasic calcium phosphate/ hydrosoluble polymer composites: a new concept for bone and dental substitution biomaterials; Bone; 25; 2:S1; 595-615

The invention claimed is:

1. An oral acid-sensing device configured for fixation to a surface of a tooth within the oral cavity of a subject, the device comprising:
   a top erodible layer comprising an erodible material; and an indicator;
   wherein the erodible material comprises a calcium phosphate composition;
   wherein the erodible material has a dissolution rate in an acidic medium which is at least 10 times greater than the dissolution rate of natural dental enamel in the same acidic medium; and/or
   wherein the erodible layer has a rate of color change due to dissolution of the erodible material which is greater than the rate of color change produced in natural dental enamel by the same acidic medium; and
   wherein erosion of the top erodible layer provides a visual response from the indicator.

2. A device according to claim 1, which is a device comprising:
   a top erodible layer, formed of an erodible material; and an indicator;
   wherein the erodible material has a dissolution rate in an acidic medium which is at least twenty times faster than the dissolution rate of natural dental enamel in the same acidic medium;
   and wherein erosion of the top erodible layer provides a visual response from the indicator.

3. A device according to claim 1, wherein the erodible layer itself serves as the indicator by producing a visible change as a result of its erosion/dissolution.

4. A device according to claim 1, wherein the indicator is comprised in a separate indicator layer, positioned beneath the top erodible layer, wherein erosion of the top erodible layer reveals the indicator layer, thus providing the visual response.

5. A device according to claim 1, wherein the device comprises at least one further erodible layer, each of said layers being formed of an erodible material having a dissolution rate in an acidic medium which is at least twenty times faster than the dissolution rate of natural dental enamel in the same acidic medium.

6. A device according to claim 1, wherein the device comprises multiple erodible layers;
   wherein each of said erodible layers optionally comprises an indicator;
   wherein the indicators in each layer may be the same or different; and optionally also comprising a separate indicator layer which does not comprise calcium phosphate, said layer being disposed beneath the erodible layers.

7. A device according to claim 1, wherein the erodible material in at least one of the erodible layers comprises a pH sensitive polymer.

8. A device according to claim 1, wherein the erodible material has a dissolution rate in the acidic medium which is at least fifty times as fast as the dissolution rate of natural dental enamel in the same acidic medium.

9. A device according to claim 8, wherein the erodible material has a dissolution rate in said mineral acid which is at least 10 times faster than its dissolution rate in organic acids, under comparable conditions.

10. A device according to claim 1, wherein the calcium phosphate composition is selected from the group consisting of monocalcium phosphate, monocalcium phosphate monohydrate, dicalcium phosphate, tricalcium phosphate, $\alpha$-tricalcium phosphate, $\beta$-tricalcium phosphate, fluoroapatite, hydroxyapatite, octacalcium phosphate, tetracalcium phosphate and mixtures thereof.

11. A device according to claim 10 wherein the calcium phosphate contains ionic substitutions.

12. A device according to claim 10, wherein the calcium phosphate composition has a density between 1.2 g/mm$^3$ and 3.18 g/mm$^3$ and/or a mean particle diameter between 2 $\mu$m and 100 $\mu$m.

13. A device according to claim 10, wherein the calcium phosphate composition has a calcium: phosphate ratio of less than 1.67:1.

14. A device according to claim 1 wherein the erodible layer further comprises a binder.

15. A device according to claim 1, wherein the device further comprises a bracket.

16. A device according to claim 1, wherein the indicator (s) are independently selected from dyes, pigments, opacifiers and fluorescent labels.

17. A method of detecting acid in the oral cavity and/or of detecting pathological tooth erosion, comprising the steps of:
   a) applying an oral acid-sensing device as defined in claim 1 to a tooth surface within the oral cavity of a subject; and
   b) monitoring the device, over a suitable time period, to determine the response from the indicator.

18. The method of claim 17 further comprising the step of:
   c) determining the presence or absence of acid in the oral cavity; and/or further comprising the step of:
   d) determining the presence or absence of pathological tooth erosion.

19. A method of diagnosing a disease or condition characterised by pathological erosive tooth wear and/or characterised by the presence of acid within the oral cavity, said method comprising the steps of:
   a) applying an oral acid-sensing device as defined in claim 1 to a tooth surface within the oral cavity of a subject; and
   b) monitoring the device, over a suitable time period, to determine the response from the indicator.

20. The method of claim 19, further comprising the step of:
   d) determining the presence or absence of acid in the oral cavity; and/or further comprising the step of: determining the presence or absence of pathological tooth erosion; and/or further comprising the step of:
   e) determining the presence or absence of said disease or condition.

21. The method of claim 20, wherein the disease or condition is selected from: gastro-oesophageal reflux disease, extra-oesophageal reflux disease, chronic cough, chronic obstructive pulmonary disease, severe asthma, bulimia, and erosive tooth wear.

22. The method of claim 20, wherein the disease or condition is gastro-oesophageal reflux disease.

23. The method of claim 19, wherein the acid is or comprises a mineral acid.

24. The method of claim 17, wherein the time period for monitoring is between 4 h and 28 days.

25. The method of claim 17, wherein a food diary of the subject is kept for the duration of the test period.

\* \* \* \* \*